(12) United States Patent
Kosemund et al.

(10) Patent No.: US 9,884,849 B2
(45) Date of Patent: Feb. 6, 2018

(54) FLUORINATED BENZOFURANYL-PYRIMIDINE DERIVATIVES CONTAINING A SULFOXIMINE GROUP

(71) Applicant: Bayer Pharma Aktiengesellschaft, Berlin (DE)

(72) Inventors: Dirk Kosemund, Berlin (DE); Ulrich Lücking, Berlin (DE); Gerhard Siemeister, Berlin (DE); Arne Scholz, Berlin (DE); Philip Lienau, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/519,076

(22) PCT Filed: Oct. 14, 2015

(86) PCT No.: PCT/EP2015/073733
§ 371 (c)(1),
(2) Date: Apr. 13, 2017

(87) PCT Pub. No.: WO2016/059086
PCT Pub. Date: Apr. 21, 2016

(65) Prior Publication Data
US 2017/0217938 A1    Aug. 3, 2017

(30) Foreign Application Priority Data
Oct. 16, 2014    (EP) ..................................... 14189235

(51) Int. Cl.
| C07D 405/04 | (2006.01) |
| A61K 31/506 | (2006.01) |
| C07D 405/10 | (2006.01) |
| C07D 239/42 | (2006.01) |

(52) U.S. Cl.
CPC .......... *C07D 405/10* (2013.01); *A61K 31/506* (2013.01); *C07D 239/42* (2013.01); *C07D 405/04* (2013.01)

(58) Field of Classification Search
CPC ... C07D 239/42; C07D 405/04; A61K 31/506
USPC .......................................... 544/331; 514/275
See application file for complete search history.

(56) References Cited

U.S. PATENT DOCUMENTS

| 2004/0209895 A1 | 10/2004 | Luecking et al. |
| 2005/0176743 A1 | 8/2005 | Luecking et al. |
| 2010/0184789 A1 | 7/2010 | Wabnitz et al. |
| 2011/0028492 A1 | 2/2011 | Barsanti et al. |
| 2011/0306602 A1 | 12/2011 | Wabnitz et al. |

FOREIGN PATENT DOCUMENTS

| EP | 2527332 | 11/2012 |
| WO | WO-02059110 | 8/2002 |
| WO | WO-2005037800 | 4/2005 |
| WO | WO-2006064251 | 6/2006 |
| WO | WO-2008028590 | 3/2008 |
| WO | WO-2008060248 | 5/2008 |
| WO | WO-2008079918 | 7/2008 |
| WO | WO-2008079933 | 7/2008 |
| WO | WO-2008129070 | 10/2008 |
| WO | WO-2008129071 | 10/2008 |
| WO | WO-2008129080 | 10/2008 |
| WO | WO-2008132138 | 11/2008 |
| WO | WO-2009029998 | 3/2009 |
| WO | WO-2009118567 | 10/2009 |
| WO | WO-2011116951 | 9/2011 |
| WO | WO-2012117059 | 9/2012 |
| WO | WO 2013/037894 | * 3/2013 |
| WO | WO-2013037894 | 3/2013 |
| WO | WO-2013037896 | 3/2013 |
| WO | WO-2014060376 | 4/2014 |
| WO | WO-2014076028 | 5/2014 |

(Continued)

OTHER PUBLICATIONS

Simone, Oncology: Introduction, Cecil Textbook of Medicine, 20th Edition, vol. 1, pp. 1004-101 O, 1996.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*

(Continued)

*Primary Examiner* — Deepak Rao
(74) *Attorney, Agent, or Firm* — Morrison & Foerster LLP

(57) ABSTRACT

The present invention relates to fluorinated benzofuranyl-pyrimidine derivatives containing a sulfoximine group of general formula (I) as described and defined herein, and methods for their preparation, their use for the treatment and/or prophylaxis of disorders, in particular of hyperproliferative disorders and/or virally induced infectious diseases and/or of cardiovascular diseases. The invention further relates to intermediate compounds useful in the preparation of said compounds of general formula (I).

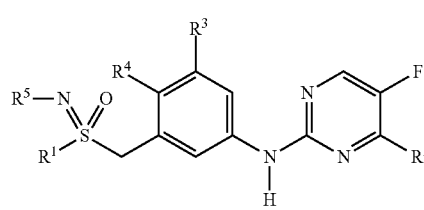

(Continued)

23 Claims, No Drawings

(56) References Cited

FOREIGN PATENT DOCUMENTS

| WO | WO-2014076091 | 5/2014 |
|---|---|---|
| WO | WO-2015001021 | 1/2015 |
| WO | WO-2015136028 | 9/2015 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Razonable et al., PubMed Abstract (Herpes 10(3):60-5), 2003.*
Blain et al., Differential Interaction of the Cyclin-dependent Kinase (Cdk) Inhibitor p27Kip1 with Cyclin A-Cdk2 nad Cyclin D2-Cdk4, The Journal of Biological Chemistry, vol. 272, No. 41, pp. 25863-25872, 1997.*
LuValle et al., Cell Cycle Control in Growth Plate, Frontiers in Biosciences, 5, d493-503, May 2000.*
Allenmark, S. et al. (1983). "Enantioselective Liquid Chromatographic Retention of a Series of Sulfoxides and N-substituted Sulfoximines on Chiral Stationary Phases," *Acta Chemica Scandinavica B* 37: 325-328.
Bark-Jones, S.J. et al. (2006). "EBV EBNA 2 stimulates CDK9-dependent transcription and RNA polymerase II phosphorylation on serine 5," *Oncogene* 25: 1775-1785.
Barnes, A.C. et al. (1979). "Pharmacologically Active Sulfoximides: 5-Hexyl-7-(S-methylsulfonimidoyl)xanthone-2-carboxylic Acid, a Potent Antiallergic Agent," *Journal of Medicinal Chemistry* 22(4): 418-424.
Bauer, V.J. et al. (Oct. 1966). "The Reactions of Carbamoyl Azides with Sulfur Nucleophiles," *Journal of Organic Chemistry* 31: 3440-3441.
Berge, S.M. et al. (Jan. 1977). "Pharmaceutical Salts," *Journal of Pharmaceutical Sciences* 66(1): 1-19.
Bolm, C. et al. (1998). "Palladium-Catalyzed Carbon-Nitrogen Bond Formation: A Novel, Catalytic Approach towards N-Arylated Sulfoximines," *Tetrahedron Letters* 39: 5731-5734.
Bolm, C. et al. (2000). "Palladium-Catalyzed N-Arylation of Sulfoximines with Aryl Bromides and Aryl Iodides," *Journal of Organic Chemistry* 65: 169-175.
Bolm, C. et al. (Feb. 2000). "Catalytic Coupling of Aryl Sulfonates with $sp^2$-Hybridized Nitrogen Nucleophiles: Palladium- and Nickel-catalyzed Synthesis of N-Aryl Sulfoximines," *Synthesis* 7: 911-913.
Bolm, C. et al. (2001). "Synthesis of Pseudopeptides with Sulfoximines as Chiral Backbone Modifying Elements," *Chem. Eur. J.* 7(5): 1118-1128.
Bolm, C. et al. (2002). "A Mild Synthetic Procedure for the Preparation of N-Alkylated Sulfoximines," *Synthesis* 7: 879-887.
Cho, G.Y., et al. (2005). "Synthesis and Palladium-Catalyzed Coupling Reaction of Enantiopure p-Bromophenyl Methyl Sulfoximine," *J. Org. Chem.* 70(6): 2346-2349.
Cho, S. et al. (May 1, 2010). "CYCLINg through transcription Posttranslational modification of P-TEFb regulate transcription elongation," *Cell Cycle* 9(9): 1697-1705.
Copeland, R. A. et al. (2006). "Drug-target residence time and its implications for lead optimization," *Nature Reviews Drug Discovery* 5: 730-739.
Craig, D. et al. (1995). " Asymmetric Intramolecular Diels-Alder Reactions of Sulfoximine-activated Trienes," *Tetrahedron* 51(21): 6071-6098.
Cram, D.J. (Dec. 16, 1970). "Stereochemistry of Sulfur Compounds. I. Stereochemical Reactions Cycles Involving an Open Chain Sulfoxide, Sulfimide, and Sulfoximide," *Journal of the American Chemical Society* 92(25): 7369-7384.
De Meijere, A. et al. (2004). "Metal-Catalyzed Cross-Coupling Reactions," *WILEY-VCH Verlag GmbH & Co. KGaA*, Weinheim, pp. 83-91.
Dey, A. et al. (Aug. 1, 2007). "HEXIM1 and the Control of Transcription Elongation from Cancer and Inflammation to AIDS and Cardiac Hypertrophy," *Cell Cycle* 6(15): 1856-1863.
Füger, B. et al. (2009). "Ring-Closing Enyne Metathesis (RCEYM) for the Synthesis of Cyclic Sulfoximines," *Synlett* 10: 1601-1604.
Hackenberger, C.P.R., et al. (2004). "Synthetic and Spectroscopic Investigation of N-Acylated Sulfoximines," *Chem. Eur. J.* 10: 2942-2952.
He, N. et al. (Mar. 14, 2008). "A La-Related Protein Modulates 7SK snRNP Integrity to Suppress P-TEFb-Dependent Transcriptional Elongation and Tumorigenesis," *Molecular Cell* 29: 588-599.
International Search Report dated Nov. 19, 2015 for PCT Application No. PCT/EP2015/073733, filed on Oct. 14, 2015, 4 pages.
Johnson, C.R. (Nov. 4, 1970). "Preparation and Synthetic Applications of (Dimethylamino)phenyloxosulfonium Methylide," *Journal of the American Chemical Society* 92(22): 6594-6598.
Johnson, C.R. (1978). "Preparation of α-Halo Sulfoximines," *Journal of Organic Chemistry* 43(21): 4136-4140.
Johnson, C.R. et al. (1993). "Alkylation of Sulfoximines and Related Compounds at the Imino Nitrogen under Phase-Transfer Conditions," *Journal of Organic Chemistry* 58(7): 1922-1923.
Jones, M.R. et al. (Apr. 3, 1974). "Stereochemisty of Sulfur Compounds. VII. Course of Substitution at Sulfur Attached to Four Different Ligands," *Journal of the American Chemical Society* 96(7): 2183-2190.
Mancheño, O.G. et al. (2007). "Synthesis of N-(1H)-Tetrazole Sulfoximines," *Organic Letters* 9(15) 2951-2954.
Okamura, H. et al. (2004). "Rhodium-Catalyzed Imination of Sulfoxides and Sulfides: Efficient Preparation of N-Unsubstituted Sulfoximines and Sulfilimines," *Organic Letters* 6(8): 1305-1307.
Polla, M.O. et al. (2004). "Design and synthesis of potent, orally active, inhibitors of carboxypeptidase U (TAFIa)," *Bioorganic & Medicinal Chemistry Letters* 12: 1151-1175.
Sammond, D.M. et al. (2005). "Discovery of a novel and potent series of dianilinopyrimidineurea and urea isostere inhibitors of VEGFR2 tyrosine kinase," *Bioorganic & Medicinal Chemistry Letters* 15: 3519-3523.
Sauer, D.T. et al. (1972). "Bis(perfluoroalkyl)sulfur Oxyimines and Silver Bis(trifluoromethyl)sulfur Oxyimine," *Inorganic Chemistry* 11(2): 238-242.
Stoss, P. et al. (1978). "Transannulare Acylwanderungen in Cyclischen Sulfoximiden," *Chem. Ber.* 111: 1453-1463.
Wang, S. et al. (2008). "Cyclin-dependent kinase 9: a key transcriptional regulator and potential drug target in oncology, virology and cardiology," *Trends in Pharmacological Sciences* 29(6): 302-313.
Wang, S. et al. (2010). "Discovery and Characterization of 2-Anilino-4-(Thiazol-5-yl)Pyrimidine Transcriptional CDK Inhibitors as Anticancer Agents," *Chemistry & Biology* 17: 1111-1121.
Yang, Z. et al. (Aug. 19, 2005). "Recruitment of P-TEFb for Stimulation of Transcriptional Elongation by the Bromodomain Protein Brd4," *Molecular Cell* 19: 535-545.
Zhou, M. et al. (Dec. 2004). "Coordination of Transcription Factor Phosphorylation and Histone Methylation by the P-TEFb Kinase during Human Immunodeficiency Virus Type 1 Transcription," *Journal of Virology* 78(24): 13522-13533.
Zhou, Q. et al. (Sep. 2006). "The Yin and Yang of P-TEFb Regulation: Implications for Human Immunodeficiency Virus Gene Expression and Global Control of Cell Growth and Differentiation," *Microbiology and Molecular Biology Reviews* 70(3): 646-659.

* cited by examiner

FLUORINATED BENZOFURANYL-PYRIMIDINE DERIVATIVES CONTAINING A SULFOXIMINE GROUP

CROSS REFERENCE TO RELATED APPLICATIONS

This application is the national stage of International Application No. PCT/EP2015/073733, filed internationally Oct. 14, 2015, which claims the benefit of European Application No. 14189235.6, filed Oct. 16, 2014, the disclosures of which are hereby incorporated by reference in their entireties for all purposes.

The present invention relates to fluorinated benzofuranyl-pyrimidine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNA polymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK). Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/dephosphorylation, ubiquitination, and acetylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance. Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO 2009118567 discloses pyrimidine and [1,3,5]triazine derivatives as protein kinase inhibitors, in particular CDK2, CDK7 and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1,3,5-triazin-2-amines as selective CDK9 inhibitors. EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heterorayl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO 2011077171 discloses 4,6-disubstituted aminopyrimidine derivatives as inhibitors of CDK9.

WO 2014031937 discloses 4,6-disubstituted aminopyrimidine derivatives as inhibitors of CDK9.

WO 2013037896 discloses disubstituted 5-fluoropyrimidines as selective inhibitors of CDK9.

WO 2013037894 discloses disubstituted 5-fluoropyrimidine derivatives containing a sulfoximine group as selective inhibitors of CDK9.

WO 2014060376 discloses substituted 4-(ortho)-fluorophenyl-5-fluoropyrimidin-2-yl amine derivatives containing a sulfone group as selective inhibitors of CDK9.

WO 2014060375 discloses substituted 5-fluoro-N-(pyridin-2-yl)pyridin-2-amine derivatives containing a sulfone group as selective inhibitors of CDK9.

WO 2014060493 discloses substituted N-(pyridin-2-yl) pyrimidin-4-amine derivatives containing a sulfone group as selective inhibitors of CDK9.

WO 2014076028 discloses substituted 4-(ortho)-fluorophenyl-5-fluoropyrimidin-2-yl amine derivatives containing a sulfoximine group as selective inhibitors of CDK9.

WO 2014076091 discloses substituted 5-fluoro-N-(pyridin-2-yl)pyridin-2-amine derivatives containing a sulfoximine group as selective inhibitors of CDK9.

WO 2014076111 discloses substituted N-(pyridin-2-yl) pyrimidin-4-amine derivatives containing a sulfoximine group as selective inhibitors of CDK9.

WO 2015001021 discloses 5-fluoro-N-(pyridin-2-yl)pyridin-2-amine derivatives containing a sulfoximine group as selective inhibitors of CDK9.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618,968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBK1 and/or IKK epsilon. The specific examples mainly focus on compounds having a pyrimidine core.

WO2012142329 concerns amino-pyrimidine compounds as inhibitors of TBK1 and/or IKK epsilon.

WO2012139499 discloses urea substituted anilino-pyrimidines as inhibitors of various protein kinases.

WO2014106762 discloses 4-pyrimidinylamino-benzenesulfonamide derivatives, differing from the compounds of the present invention inter alia through the sulfonamido moiety attached to the aniline portion, as inhibitors of polo-like kinase-1.

Despite the fact that various inhibitors of CDKs are known, there remains a need for selective CDK9 inhibitors to be used for the treatment of diseases such as hyperproliferative diseases, viral diseases, and/or diseases of the heart, which offer one or more advantages over the compounds known from prior art, such as:
  improved activity and/or efficacy
  beneficial kinase selectivity profile according to the respective therapeutic need
  improved side effect profile, such as fewer undesired side effects, lower intensity of side effects, or reduced (cyto)toxicity
  improved physicochemical properties, such as solubility in water and body fluids
  improved pharmacokinetic properties, allowing e.g. for dose reduction or an easier dosing scheme
  easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E, preferably at high ATP concentrations, e.g. as determined using Method 1b. "CDK9/CycT1 high ATP kinase assay" and Method 2b. "CDK2/CycE high ATP assay", infra.

Another object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors which show as an increased apparent Caco-2 permeability ($P_{app}$ A-B) across Caco-2 cell monolayers, and/or a decreased efflux ratio (efflux ratio=$P_{app}$ B-A/$P_{app}$ A-B) from the basal to apical compartment across Caco-2 cell monolayers, compared to the compounds known from prior art.

Another particular object of the invention is to provide CDK9 kinase inhibitors, which show an improved anti-proliferative activity in tumor cell lines such as HeLa, HeLa-MaTu-ADR, NCI-H460, DU145, Caco-2, B16F10, A2780 or MOLM-13, compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, preferably at high ATP concentrations, and/or which show an increased potency to inhibit CDK9 activity and/or which show as an increased apparent Caco-2 permeability ($P_{app}$ A-B) across Caco-2 cell monolayers, and/or a decreased efflux ratio (efflux ratio=$P_{app}$ B-A/$P_{app}$ A-B) from the basal to apical compartment across Caco-2 cell monolayers, and/or which show an improved anti-proliferative activity in tumor cell lines such as HeLa, HeLa-MaTu-ADR, NCI-H460, DU145, Caco-2, B16F10, A2780 or MOLM-13, and/or which show an increased potency to inhibit CDK9 activity at high ATP concentrations compared to the compounds known from prior art.

The present invention relates to compounds of general formula (I)

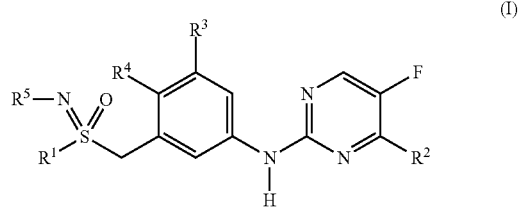

wherein
$R^1$ represents a group selected from $C_1$-$C_6$-alkyl-, $C_3$-$C_7$-cycloalkyl-, heterocyclyl-, phenyl-, heteroaryl-, phenyl-$C_1$-$C_3$-alkyl- and heteroaryl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;

$R^2$ represents the group

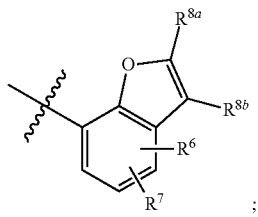

$R^3$, $R^4$ represent, independently from each other, a group selected from a hydrogen atom, fluoro atom, chloro atom, bromo atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —$C(O)R^9$, —$C(O)OR^9$, —$S(O)_2R^9$, —$C(O)NR^{10}R^{11}$, —$P(O)(OR^{12})_2$, —$CH_2OP(OR^{12})_2$, $C_1$-$C_6$-alkyl-, $C_3$-$C_7$-cycloalkyl-, heterocyclyl-, phenyl-, heteroaryl-, wherein said $C_1$-$C_6$-alkyl-, $C_3$-$C_7$-cycloalkyl-, heterocyclyl-, phenyl- or heteroaryl- group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^9$ represents a group selected from $C_1$-$C_6$-alkyl-, halo-$C_1$-$C_3$-alkyl-, $C_3$-$C_7$-cycloalkyl-, heterocyclyl-, phenyl-, benzyl- and heteroaryl-, wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from a hydrogen atom, $C_1$-$C_6$-alkyl-, $C_3$-$C_7$-cycloalkyl-, heterocyclyl-, phenyl-, benzyl- and heteroaryl-, wherein said $C_1$-$C_6$-alkyl-, $C_3$-$C_7$-cycloalkyl-, heterocyclyl-, phenyl-, benzyl- or heteroaryl-group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine;

$R^{12}$ represents a group selected from a hydrogen atom, $C_1$-$C_4$-alkyl- and benzyl-;

and the enantiomers, diastereomers, salts, solvates or salts of solvates thereof.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents such as lower alkylhalides such as methyl-, ethyl-, propyl-, and butylchlorides, -bromides and -iodides; dialkylsulfates such as dimethyl-, diethyl-, dibutyl- and diamylsulfates, long chain halides such as decyl-, lauryl-, myristyl- and stearylchlorides, -bromides and -iodides, aralkylhalides such as benzyl- and phenethylbromides and others. Examples of suitable quarternary ammonium ions are tetramethylammonium, tetraethylammonium, tetra(n-propyl)ammonium, tetra (n-butyl)ammonium, or N-benzyl-N, N,N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The term "halogen atom" or "halo" represents fluorine, chlorine, bromine and iodine, particularly chlorine or fluorine, preferably fluorine.

The term "alkyl-" represents a linear or branched alkyl radical having the number of carbon atoms specifically indicated, e.g. $C_1$-$C_{10}$ one, two, three, four, five, six, seven, eight, nine or ten carbon atoms, e.g. methyl-, ethyl-, n-propyl-, isopropyl-, n-butyl-, isobutyl-, sec-butyl-, tert-butyl-, pentyl-, isopentyl-, hexyl-, heptyl-, octyl-, nonyl-, decyl-, 2-methylbutyl-, 1-methylbutyl-, 1-ethylpropyl-, 1,2-dimethylpropyl-, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, or 1,2-dimethylbutyl-. If the number of carbon atoms is not specifically indicated the term "alkyl-" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl-"), e.g. methyl-, ethyl-, n-propyl-, isopropyl-, n-butyl-, tert-butyl-, pentyl-, isopentyl-, hexyl-, 2-methylbutyl-, 1-methylbutyl-, 1-ethylpropyl-, 1,2-dimethylpropyl-, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, or 1,2-dimethylbutyl-.

Preferably, the alkyl group has 1, 2 or 3 carbon atoms ("$C_1$-$C_3$-alkyl-"), methyl-, ethyl-, n-propyl- or isopropyl-.

The term "$C_3$-$C_7$-cycloalkyl-" is to be understood as preferably meaning a saturated or partially unsaturated, monovalent, monocyclic hydrocarbon ring which contains 3, 4, 5, 6 or 7 carbon atoms. Said $C_3$-$C_7$-cycloalkyl- group is for example, a monocyclic hydrocarbon ring, e.g. a cyclopropyl-, cyclobutyl-, cyclopentyl-, cyclohexyl- or cycloheptyl- group. Said cycloalkyl-ring is non-aromatic but can optionally contain one or more double bonds e.g. cycloalkenyl-, such as a cyclopropenyl-, cyclobutenyl-, cyclopentenyl-, cyclohexenyl- or cycloheptenyl- group, wherein the bond between said ring with the rest of the molecule may be to any carbon atom of said ring, be it saturated or unsaturated. Particularly, said cycloalkyl- group is a $C_4$-$C_6$-cycloalkyl-, a $C_5$-$C_6$-cycloalkyl- or a cyclohexyl- group.

The term "$C_3$-$C_5$-cycloalkyl-" is to be understood as preferably meaning a saturated, monovalent, monocyclic hydrocarbon ring which contains 3, 4 or 5 carbon atoms. In particular said $C_3$-$C_5$-cycloalkyl-group is a monocyclic hydrocarbon ring such as a cyclopropyl-, cyclobutyl- or cyclopentyl- group. Preferably said "$C_3$-$C_5$-cycloalkyl-" group is a cyclopropyl- group.

The term "$C_3$-$C_6$-cycloalkyl-" is to be understood as preferably meaning a saturated, monovalent, monocyclic hydrocarbon ring which contains 3, 4, 5 or 6 carbon atoms.

In particular said $C_3$-$C_5$-cycloalkyl- group is a monocyclic hydrocarbon ring such as a cyclopropyl-, cyclobutyl-, cyclopentyl- or cyclohexyl- group.

The term "heterocyclyl-" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl-" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. A $C_3$-$C_9$-heterocyclyl- is to be understood as meaning a heterocyclyl- which contains 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl-, azetidinyl-, tetrahydrofuranyl-, pyrrolidinyl-, 1,3-dioxolanyl-, imidazolidinyl-, pyrazolidinyl-, oxazolidinyl-, isoxazolidinyl-, 1,4-dioxanyl-, pyrrolinyl-, tetrahydropyranyl-, piperidinyl-, morpholinyl-, 1,3-dithianyl-, thiomorpholinyl-, piperazinyl-, or chinuclidinyl- group. Optionally, said heterocyclic ring can contain one or more double bonds, e.g. 4H-pyranyl-, 2H-pyranyl-, 2,5-dihydro-1H-pyrrolyl-, 1,3-dioxolyl-, 4H-1,3,4-thiadiazinyl-, 2,5-dihydrofuranyl-, 2,3-dihydrofuranyl-, 2,5-dihydrothienyl-, 2,3-dihydrothienyl-, 4,5-dihydrooxazolyl-, 4,5-dihydroisoxazolyl-, or 4H-1,4-thiazinyl- group, or, it may be benzo fused.

Particularly, a $C_3$-$C_7$-heterocyclyl- is to be understood as meaning a heterocyclyl- which contains 3, 4, 5, 6, or 7 carbon atoms and additionally at least one heteroatom as ring atoms. Accordingly, in case of one heteroatom the ring is 4- to 8-membered, in case of two heteroatoms the ring is 5- to 9-membered and in case of three heteroatoms the ring is 6- to 10-membered.

Particularly, a $C_3$-$C_6$-heterocyclyl- is to be understood as meaning a heterocyclyl- which contains 3, 4, 5 or 6 carbon atoms and additionally at least one heteroatom as ring atoms. Accordingly, in case of one heteroatom the ring is 4- to 7-membered, in case of two heteroatoms the ring is 5- to 8-membered and in case of three heteroatoms the ring is 6- to 9-membered.

Particularly, the term "heterocyclyl-" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy-, ethoxy-, n-propoxy-, iso-propoxy-, n-butoxy-, iso-butoxy-, tert-butoxy-, sec-butoxy-, pentyloxy-, iso-pentyloxy-, n-hexyloxy- group, or an isomer thereof. Particularly, the "$C_1$-$C_6$-alkoxy-" group is a "$C_1$-$C_4$-alkoxy-", a "$C_1$-$C_3$-alkoxy-", a methoxy-, ethoxy-, or propoxy- group, preferably a methoxy-, ethoxy- or propoxy- group. Further preferred is a "$C_1$-$C_2$-alkoxy-" group, particularly a methoxy- or ethoxy- group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy- particularly a "$C_1$-$C_2$-fluoroalkoxy-" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino- und N-n-Hexyl-N-methylamino-.

The term "cyclic amine" is to be understood as preferably meaning a saturated, monocyclic group with 4 to 10, preferably 4 to 7 ring atoms, of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl- groups.

The term "halo-$C_1$-$C_3$-alkyl-" is to be understood as preferably meaning a linear or branched, saturated, monovalent hydrocarbon group in which the term "$C_1$-$C_3$-alkyl-" is defined supra, and in which one or more hydrogen atoms is replaced by a halogen atom, identically or differently, i.e. one halogen atom being independent from another. Particularly, said halogen atom is fluorine. Preferably, said halo-$C_1$-$C_3$-alkyl-group is a fluoro-$C_1$-$C_3$-alkyl- group, such as for example —$CF_3$, —$CHF_2$, —$CH_2F$, —$CF_2CF_3$, or —$CH_2CF_3$, more preferably it is —$CF_3$.

The term "phenyl-$C_1$-$C_3$-alkyl-" is to be understood as preferably meaning a phenyl- group, in which one of the hydrogen atoms is replaced by a $C_1$-$C_3$-alkyl- group, as defined supra, that links the phenyl-$C_1$-$C_3$-alkyl-group to the rest of the molecule. Particularly, the "phenyl-$C_1$-$C_3$-alkyl-" is a phenyl-$C_1$-$C_2$-alkyl-, preferably it is a benzyl- group.

The term "heteroaryl-" is to be understood as preferably meaning a monovalent, aromatic ring system having 5, 6, 7, 8, 9, 10, 11, 12, 13 or 14 ring atoms (a "5- to 14-membered heteroaryl-" group), particularly 5 (a "5-membered heteroaryl-") or 6 (a "6-membered heteroaryl-") or 9 (a "9-membered heteroaryl-") or 10 ring atoms (a "10-membered heteroaryl-"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl- is selected from thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl- etc., and benzo derivatives thereof, such as, for example, benzofuranyl-, benzothienyl-, benzoxazolyl-, benzisoxazolyl-, benzimidazolyl-, benzotriazolyl-, indazolyl-, indolyl-, isoindolyl-, etc.; or pyridyl-, pyridazinyl-, pyrimidinyl-, pyrazinyl-, triazinyl-, etc., and benzo derivatives thereof, such as, for example, quinolinyl-, quinazolinyl-, isoquinolinyl-, etc.; or azocinyl-, indolizinyl-, purinyl-, etc., and benzo derivatives thereof; or cinnolinyl-, phthalazinyl-, quinazolinyl-, quinoxalinyl-, naphthyridinyl-, pteridinyl-, carbazolyl-, acridinyl-, phenazinyl-, phenothiazinyl-, phenoxazinyl-, xanthenyl-, or oxepinyl-, etc. Preferably, heteroaryl- is selected from monocyclic heteroaryl-, 5-membered heteroaryl- or 6-membered heteroaryl-.

The term "5-membered heteroaryl-" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl-" is selected from thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-.

The term "6-membered heteroaryl-" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl-" is selected from pyridyl-, pyridazinyl-, pyrimidinyl-, pyrazinyl-, triazinyl-.

The term "heteroaryl-$C_1$-$C_3$-alkyl-" is to be understood as preferably meaning a heteroaryl-, a 5-membered heteroaryl- or a 6-membered heteroaryl- group, each as defined supra, in which one of the hydrogen atoms is replaced by a $C_1$-$C_3$-alkyl- group, as defined supra, that links the heteroaryl-$C_1$-$C_3$-alkyl- group to the rest of the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy-, p-toluenesulfonyloxy-, trifluoromethanesulfonyloxy-, nonafluorobutanesulfonyloxy-, (4-bromo-benzene)sulfonyloxy-, (4-nitro-benzene)sulfonyloxy-, (2-nitro-benzene)-sulfonyloxy-, (4-isopropyl-benzene)sulfonyloxy-, (2,4,6-tri-isopropyl-benzene)-sulfonyloxy-, (2,4,6-trimethyl-benzene)sulfonyloxy-, (4-tertbutyl-benzene)sulfonyloxy-, benzenesulfonyloxy-, and (4-methoxy-benzene) sulfonyloxy-.

The term "$C_1$-$C_{10}$", as used throughout this text, e.g. in the context of the definition of "$C_1$-$C_{10}$-alkyl-" is to be understood as meaning an alkyl- group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl-", "$C_1$-$C_6$-alkoxy-" is to be understood as meaning an alkyl- group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl-", "$C_1$-$C_3$-alkoxy-" or "$C_1$-$C_3$-fluoroalkoxy-" is to be understood as meaning an alkyl- group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl-", is to be understood as meaning a cycloalkyl- group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$.

Further, as used herein, the term "$C_3$-$C_7$", as used throughout this text, e.g. in the context of the definition of "$C_3$-$C_7$-cycloalkyl-", is to be understood as meaning a cycloalkyl- group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⌒ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment the present invention concerns compounds of general formula (I), wherein $R^1$ represents a group selected from $C_1$-$C_6$-alkyl-, $C_3$-$C_5$-cycloalkyl-, wherein said group is optionally substituted with one substituent selected from the group of hydroxy, halo-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(O)(OH)$_2$, —C(O)OH, —C(O)NH$_2$;

$R^2$ represents the group

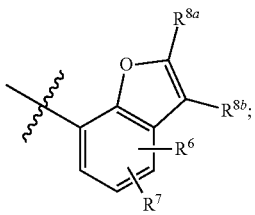

$R^3$ represents a hydrogen atom, a fluoro atom or chloro atom, a —SF$_5$ group, a $C_1$-$C_3$-alkyl- group or a fluoro-$C_1$-$C_3$-alkyl- group;

$R^4$ represents a hydrogen atom or a fluoro atom;

$R^5$ represents a group selected from a hydrogen atom, cyano, —C(O)R$^9$, —C(O)OR$^9$, —S(O)$_2$R$^9$, —C(O)NR$^{10}$R$^{11}$, —P(O)(OR$^{12}$)$_2$, —CH$_2$OP(OR$^{12}$)$_2$, $C_1$-$C_6$-alkyl-, $C_3$-$C_7$-cycloalkyl-, heterocyclyl-, phenyl-, heteroaryl-,
  wherein said $C_1$-$C_6$-alkyl-, $C_3$-$C_7$-cycloalkyl-, heterocyclyl-, phenyl- or heteroaryl- group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^9$ represents a group selected from $C_1$-$C_6$-alkyl-, halo-$C_1$-$C_3$-alkyl-, $C_3$-$C_7$-cycloalkyl-, heterocyclyl-, phenyl-, benzyl- and heteroaryl-,
  wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from a hydrogen atom, $C_1$-$C_6$-alkyl-, $C_3$-$C_7$-cycloalkyl-, heterocyclyl-, benzyl-, phenyl- and heteroaryl-,
  wherein said $C_1$-$C_6$-alkyl-, $C_3$-$C_7$-cycloalkyl-, heterocyclyl-, benzyl-, phenyl- or heteroaryl-group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine;

$R^{12}$ represents a group selected from a hydrogen atom and $C_1$-$C_2$-alkyl-;

and the enantiomers, diastereomers, salts, solvates or salts of solvates thereof.

In a preferred embodiment the present invention concerns compounds of general formula (I), wherein $R^1$ represents a group selected from $C_1$-$C_6$-alkyl-, $C_3$-$C_5$-cycloalkyl-,
  wherein said group is optionally substituted with one substituent selected from the group of hydroxy, $C_1$-$C_3$-alkoxy-, —NH$_2$, alkylamino-, dialkylamino-, cyclic amines, —OP(O)(OH)$_2$;

$R^2$ represents the group

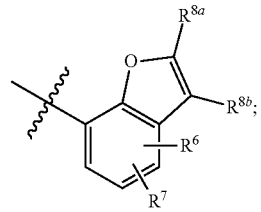

$R^3$ represents a hydrogen atom, fluoro atom or chloro atom, a —SF$_5$ group, a $C_1$-$C_3$-alkyl- group or a fluoro-$C_1$-$C_3$-alkyl- group;

$R^4$ represents a hydrogen atom or a fluoro atom;

$R^5$ represents a group selected from a hydrogen atom, cyano, —C(O)R$^9$, —C(O)OR$^9$, —C(O)NR$^{10}$R$^{11}$, —P(O)(OR$^{12}$)$_2$, —CH$_2$OP(OR$^{12}$)$_2$, $C_1$-$C_3$-alkyl-,
  wherein said $C_1$-$C_3$-alkyl group is optionally substituted with one substituent, selected from —NH$_2$, alkylamino-, dialkylamino-, and cyclic amines;

$R^6$, $R^7$ represent, independently from each other, a group selected from a hydrogen atom, a fluoro atom and a chloro atom;

$R^{8a}$, $R^{8b}$ represent, independently from each other, a group selected from a hydrogen atom, fluoro atom, chloro atom, bromo atom, cyano, methyl-, methoxy-, halomethyl-, fluoromethyl-;

$R^9$ represents a group selected from $C_1$-$C_3$-alkyl-, halo-$C_1$-$C_3$-alkyl-, and benzyl- group, the phenyl-group of which is optionally substituted with one or two substituents, identically or differently, selected from the group of halogen, $C_1$-$C_3$-alkyl-, $C_1$-$C_3$-alkoxy-, —NH$_2$, alkylamino-, dialkylamino-;

$R^{10}$, $R^{11}$ represent, independently from each other, a group selected from a hydrogen atom, $C_1$-$C_3$-alkyl-, benzyl-, or $R^{10}$ and $R^{11}$, together with the nitrogen atom they are attached to, form a cyclic amine;

$R^{12}$ represents a group selected from a hydrogen atom and methyl-, and the enantiomers, diastereomers, salts, solvates or salts of solvates thereof.

In another preferred embodiment the present invention concerns compounds of general formula (I), wherein $R^1$ represents a $C_1$-$C_6$-alkyl- group,
  wherein said group is optionally substituted with one substituent, selected from the group of $C_1$-$C_3$-alkoxy, —NH$_2$, alkylamino-, dialkylamino-, and cyclic amines;

$R^2$ represents the group

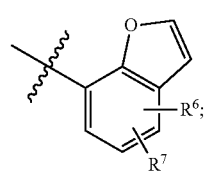

R³ represents a hydrogen atom, fluoro atom or chloro atom or a —SF₅, methyl-, ethyl- or trifluoromethyl- group;
R⁴ represents a hydrogen atom or fluoro atom;
R⁵ represents a group selected from a hydrogen atom, cyano, —C(O)R⁹, —C(O)OR⁹, —C(O)NR¹¹OR¹¹;
R⁶, R⁷ represent, independently from each other, a group selected from a hydrogen atom, fluoro atom and chloro atom;
R⁹ represents a C₁-C₃-alkyl- group, a benzyl- group, or trifluoromethyl-;
R¹⁰, R¹¹ represent, independently from each other, a group selected from a hydrogen atom, C₁-C₂-alkyl-; and the enantiomers, diastereomers, salts, solvates or salts of solvates thereof.

In a particularly preferred embodiment the present invention concerns compounds of general formula (I), wherein
R¹ represents a C₁-C₃-alkyl- group;
R² represents the group

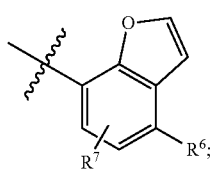

R³ represents a hydrogen atom or fluoro atom or a methyl- or —SF₅ group;
R⁴ represents a hydrogen atom;
R⁵ represents a group selected from a hydrogen atom, cyano, —C(O)R⁹, —C(O)OR⁹, —C(O)NR¹⁰R¹¹;
R⁶ represents a group selected from a hydrogen atom, fluoro atom and chloro atom,
R⁷ represents a hydrogen atom;
R⁹ represents a methyl-, ethyl- or trifluoromethyl- group;
R¹⁰ represents a C₁-C₃-alkyl- group;
R¹¹ represents a hydrogen atom;
and the enantiomers, diastereomers, salts, solvates or salts of solvates thereof.

In another particularly preferred embodiment the present invention concerns compounds of general formula (I), wherein
R¹ represents a C₁-C₃-alkyl- group;
R² represents the group

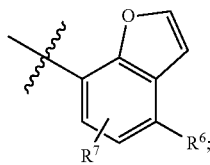

R³ represents a hydrogen atom or fluoro atom or a methyl- or —SF₅ group;
R⁴ represents a hydrogen atom;
R⁵ represents a group selected from a hydrogen atom, cyano, —C(O)R⁹, —C(O)OR⁹, —C(O)NR¹⁰R¹¹;
R⁶ represents a group selected from a hydrogen atom and a fluoro atom,
R⁷ represents a hydrogen atom;
R⁹ represents a methyl-, ethyl- or trifluoromethyl- group;
R¹⁰ represents a C₁-C₂-alkyl- group;
R¹¹ represents a hydrogen atom;
and the enantiomers, diastereomers, salts, solvates or salts of solvates thereof.

In another particularly preferred embodiment the present invention concerns compounds of general formula (I), wherein
R¹ represents a methyl- group;
R² represents the group

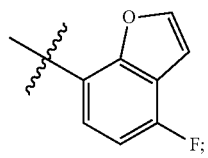 [SMILES: *c1ccc(F)c2ccoc12]

R³ represents a hydrogen atom or fluoro atom or a methyl- or —SF₅ group;
R⁴ represents a hydrogen atom;
R⁵ represents a group selected from a hydrogen atom and a cyano group;
and the enantiomers, diastereomers, salts, solvates or salts of solvates thereof.

In another embodiment the invention relates to compounds of formula (I), in which R¹ represents a group selected from C₁-C₆-alkyl-, C₃-C₇-cycloalkyl-, heterocyclyl-, phenyl-, heteroaryl-, phenyl-C₁-C₃-alkyl- and heteroaryl-C₁-C₃-alkyl-,
 wherein said group is optionally substituted with one or two or three substituents, identically or differently, selected from the group of hydroxy, cyano, halogen, halo-C₁-C₃-alkyl-, C₁-C₆-alkoxy-, C₁-C₃-fluoroalkoxy-, —NH₂, alkylamino-, dialkylamino-, acetylamino-, N-methyl-N-acetylamino-, cyclic amines, —OP(O)(OH)₂, —C(O)OH, —C(O)NH₂.

In another embodiment the invention relates to compounds of formula (I), in which R¹ represents a group selected from C₁-C₃-alkyl-, C₃-C₅-cycloalkyl-, 4- to 7-membered heterocyclyl-, phenyl-, heteroaryl-, phenyl-C₁-C₂-alkyl- and heteroaryl-C₁-C₂-alkyl-,
 wherein said group is optionally substituted with one or two or three substituents, identically or differently, selected from the group of hydroxy, cyano, halogen, halo-C₁-C₂-alkyl-, C₁-C₃-alkoxy-, C₁-C₂-fluoroalkoxy-, —NH₂, alkylamino-, dialkylamino-, acetylamino-, N-methyl-N-acetylamino-, cyclic amines.

In another embodiment the invention relates to compounds of formula (I), in which R¹ represents a group selected from C₁-C₆-alkyl-, C₃-C₅-cycloalkyl-,
 wherein said group is optionally substituted with one substituent selected from the group of hydroxy, halo-C₁-C₂-alkyl-, C₁-C₃-alkoxy-, C₁-C₂-fluoroalkoxy-, —NH₂, alkylamino-, dialkylamino-, cyclic amines, —OP(O)(OH)₂, —C(O)OH, —C(O)NH₂.

In another embodiment the invention relates to compounds of formula (I), in which R¹ represents a group selected from C₁-C₆-alkyl-, C₃-C₅-cycloalkyl-,
 wherein said group is optionally substituted with one substituent selected from the group of hydroxy, C₁-C₃-alkoxy-, —NH₂, alkylamino-, dialkylamino-, cyclic amines, —OP(O)(OH)₂.

In another embodiment the invention relates to compounds of formula (I), in which R¹ represents a group selected from methyl-, ethyl-, propan-2-yl-, tert-butyl-, cyclopropyl-, cyclohexyl- or phenyl-, wherein said group is optionally substituted with one substituent selected from the group of hydroxy or methoxy-.

In another preferred embodiment the invention relates to compounds of formula (I), in which $R^1$ represents a $C_1$-$C_6$-alkyl- group, wherein said group is optionally substituted with one substituent selected from the group of $C_1$-$C_3$-alkoxy, —$NH_2$, alkylamino-, dialkylamino-, and cyclic amines.

In another preferred embodiment the invention relates to compounds of formula (I), in which $R^1$ represents a group selected from methyl-, ethyl-, propan-2-yl-, cyclopropyl-, tert-butyl-, cyclopentyl-, cyclohexyl- or phenyl-,
wherein said group is optionally substituted with one substituent, selected from the group of $C_1$-$C_3$-alkoxy, —$NH_2$, alkylamino-, dialkylamino-, and cyclic amines.

In a particularly preferred embodiment the present invention concerns compounds of general formula (I), wherein $R^1$ represents a $C_1$-$C_3$-alkyl- group.

In another particularly preferred embodiment the present invention concerns compounds of general formula (I), wherein $R^1$ represents a methyl- group.

In another embodiment the invention relates to compounds of formula (I), in which $R^2$ represents the group

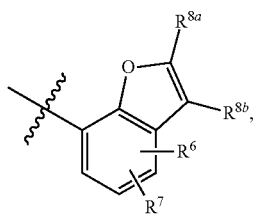

wherein
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-, and wherein
$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^2$ represents the group

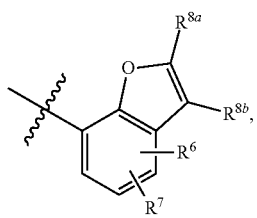

wherein
$R^6$, $R^7$ represent, independently from each other, a group selected from a hydrogen atom, a fluoro atom or a chloro atom, and wherein
$R^{8a}$, $R^{8b}$ represent, independently from each other, a group selected from a hydrogen atom, fluoro atom, chloro atom, bromo atom, cyano, methyl-, methoxy-, halomethyl-, fluoromethoxy-.

In a particularly preferred embodiment the invention relates to compounds of formula (I), in which $R^2$ represents the group

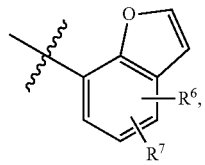

wherein
$R^6$, $R^7$ represent, independently from each other, a group selected from a hydrogen atom, fluoro atom or chloro atom.

In another particularly preferred embodiment the invention relates to compounds of formula (I), in which $R^2$ represents the group

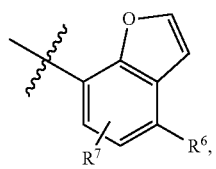

wherein
$R^6$ represents a group selected from hydrogen, a fluoro or chloro atom, and wherein
$R^7$ represents hydrogen.

In another particularly preferred embodiment the invention relates to compounds of formula (I), in which $R^2$ represents the group

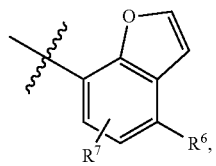

wherein
$R^6$ represents a group selected from hydrogen and a fluoro atom, and wherein
$R^7$ represents hydrogen.

In another particularly preferred embodiment the invention relates to compounds of formula (I), in which $R^2$ represents the group

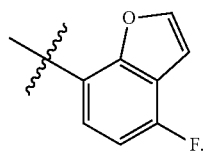 [SMILES: *c1ccc(F)c2ccoc12]

In another embodiment the invention relates to compounds of formula (I), in which $R^3$ and $R^4$ represent, independently from each other, a group selected from a hydrogen atom, fluoro atom, chloro atom, bromo atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^3$ represents a hydrogen atom, fluoro atom or chloro atom, a —$SF_5$ or $C_1$-$C_3$-alkyl- group, or a fluoro-$C_1$-$C_3$-alkyl- group, and $R^4$ represents a hydrogen atom or a fluoro atom.

In another preferred embodiment the invention relates to compounds of formula (I), in which $R^3$ represents a hydrogen atom, fluoro atom or chloro atom, or a —$SF_5$ or a methyl- group, and $R^4$ represents a hydrogen atom or a fluoro atom.

In another preferred embodiment the invention relates to compounds of formula (I), in which $R^3$ represents a hydrogen atom, fluoro atom or chloro atom, or a —$SF_5$, methyl-, ethyl- or trifluoromethyl-group, and $R^4$ represents a hydrogen atom or a fluoro atom.

In another preferred embodiment the invention relates to compounds of formula (I), in which $R^3$ represents a hydrogen atom, fluoro atom or chloro atom, or a —$SF_5$, methyl-, ethyl- or trifluoromethyl-group, and $R^4$ represents a hydrogen atom.

In another preferred embodiment the invention relates to compounds of formula (I), in which $R^3$ represents a hydrogen atom or fluoro atom, or a —$SF_5$, methyl-, ethyl- or trifluoromethyl- group, and $R^4$ represents a hydrogen atom or a fluoro atom.

In another preferred embodiment the invention relates to compounds of formula (I), in which $R^3$ represents a hydrogen atom or fluoro atom, or a —$SF_5$, methyl-, ethyl- or trifluoromethyl- group, and $R^4$ represents a hydrogen atom.

In another preferred embodiment the invention relates to compounds of formula (I), in which $R^3$ represents a —$SF_5$, methyl-, ethyl- or trifluoromethyl- group, and $R^4$ represents a hydrogen atom or a fluoro atom.

In another preferred embodiment the invention relates to compounds of formula (I), in which $R^3$ represents a methyl-, ethyl- or trifluoromethyl- group, and $R^4$ represents a hydrogen atom.

In a particularly preferred embodiment the invention relates to compounds of formula (I), in which $R^3$ represents a hydrogen atom or fluoro atom, or a —$SF_5$ or methyl- group, and $R^4$ represents a hydrogen atom or a fluoro atom.

In another particularly preferred embodiment the invention relates to compounds of formula (I), in which $R^3$ represents a hydrogen atom or fluoro atom, or a —$SF_5$ or methyl- group, and $R^4$ represents a hydrogen atom.

In another particularly preferred embodiment the invention relates to compounds of formula (I), in which $R^3$ represents a hydrogen atom, and $R^4$ represents a hydrogen atom.

In another particularly preferred embodiment the invention relates to compounds of formula (I), in which $R^3$ represents a fluoro atom, and $R^4$ represents a hydrogen atom.

In another particularly preferred embodiment the invention relates to compounds of formula (I), in which $R^3$ represents a —$SF_5$ group, and $R^4$ represents a hydrogen atom.

In another particularly preferred embodiment the invention relates to compounds of formula (I), in which $R^3$ represents a methyl- group, and $R^4$ represents a hydrogen atom.

In another embodiment the invention relates to compounds of formula (I), in which $R^3$ represents a group selected from a hydrogen atom, fluoro atom, chloro atom, —$SF_5$, $C_1$-$C_2$-alkyl-, $C_1$-$C_2$-alkoxy-, halo-$C_1$-$C_2$-alkyl-, $C_1$-$C_2$-fluoroalkoxy-.

In a preferred embodiment the invention relates to compounds of formula (I), in which $R^3$ represents a hydrogen atom, a fluoro atom or a chloro atom, a —$SF_5$ or $C_1$-$C_3$-alkyl- group or a fluoro-$C_1$-$C_3$-alkyl- group.

In another preferred embodiment the invention relates to compounds of formula (I), in which $R^3$ represents a hydrogen atom, fluoro atom or chloro atom, a —$SF_5$ or $C_1$-$C_2$-alkyl- group or a fluoro-$C_1$-$C_2$-alkyl- group.

In another preferred embodiment the invention relates to compounds of formula (I), in which $R^3$ represents a hydrogen atom, fluoro atom or chloro atom or a —$SF_5$ or methyl- group.

In another preferred embodiment the invention relates to compounds of formula (I), in which $R^3$ represents a hydrogen atom, fluoro atom or chloro atom, or a —$SF_5$, methyl-, ethyl- or trifluoromethyl-group.

In another preferred embodiment the invention relates to compounds of formula (I), in which $R^3$ represents a hydrogen atom, fluoro atom, or a —$SF_5$, methyl-, ethyl- or trifluoromethyl- group.

In another preferred embodiment the invention relates to compounds of formula (I), in which $R^3$ represents a —$SF_5$, methyl-, ethyl- or trifluoromethyl- group.

In another preferred embodiment the invention relates to compounds of formula (I), in which $R^3$ represents a —$SF_5$ or methyl- group.

In another preferred embodiment the invention relates to compounds of formula (I), in which $R^3$ represents a hydrogen atom or fluoro atom or a methyl- or —$SF_5$ group.

In another preferred embodiment the invention relates to compounds of formula (I), in which $R^3$ represents a methyl- group.

In another preferred embodiment the invention relates to compounds of formula (I), in which $R^3$ represents a —$SF_5$ group.

In another preferred embodiment the invention relates to compounds of formula (I), in which $R^3$ represents a fluoro atom.

In another preferred embodiment the invention relates to compounds of formula (I), in which $R^3$ represents a hydrogen atom.

In another embodiment the invention relates to compounds of formula (I), in which $R^4$ represents a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^4$ represents a group selected from a hydrogen atom, a fluoro atom or a chloro atom.

In a preferred embodiment the invention relates to compounds of formula (I), in which $R^4$ represents a group selected from a hydrogen atom or fluoro atom.

In another preferred embodiment the invention relates to compounds of formula (I), in which $R^4$ represents a fluoro atom.

In a particularly preferred embodiment the invention relates to compounds of formula (I), in which $R^4$ represents a hydrogen atom.

In another embodiment the invention relates to compounds of formula (I), in which $R^5$ represents a group selected from a hydrogen atom, cyano, —C(O)$R^9$, —C(O)O$R^9$, —S(O)$_2R^9$, —C(O)N$R^{10}R^{11}$, —P(O)(O$R^{12}$)$_2$, —CH$_2$OP(O$R^{12}$)$_2$, $C_1$-$C_6$-alkyl-, $C_3$-$C_7$-cycloalkyl-, heterocyclyl-, phenyl-, heteroaryl-,
  wherein said $C_1$-$C_6$-alkyl, $C_3$-$C_7$-cycloalkyl-, heterocyclyl-, phenyl- or heteroaryl- group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^5$ represents a group selected from a hydrogen atom, cyano, —C(O)$R^9$, —C(O)O$R^9$, —C(O)N$R^{10}R^{11}$, —P(O)(O$R^{12}$)$_2$, —CH$_2$OP(O$R^{12}$)$_2$, $C_1$-$C_3$-alkyl-,
  wherein said $C_1$-$C_3$-alkyl- group is optionally substituted with one substituent, selected from —NH$_2$, alkylamino-, dialkylamino-, and cyclic amines.

In a preferred embodiment the invention relates to compounds of formula (I), in which $R^5$ represents a group selected from a hydrogen atom, cyano, —C(O)$R^9$, —C(O)O$R^9$, —C(O)N$R^{10}R^{11}$.

In another preferred embodiment the invention relates to compounds of formula (I), in which $R^5$ represents a group selected from a hydrogen atom, —C(O)O$R^9$ and —C(O)N$R^{10}R^{11}$.

In another preferred embodiment the invention relates to compounds of formula (I), in which $R^5$ represents a group selected from a hydrogen atom and —C(O)N$R^{10}R^{11}$.

In another preferred embodiment the invention relates to compounds of formula (I), in which $R^5$ represents a group selected from a hydrogen atom and —C(O)O$R^9$.

In another preferred embodiment the invention relates to compounds of formula (I), in which $R^5$ represents a group selected from a hydrogen atom, cyano, —C(O)O$R^9$, —C(O)N$R^{10}R^{11}$.

In another preferred embodiment the invention relates to compounds of formula (I), in which $R^5$ represents a —C(O)$R^9$ group.

In another preferred embodiment the invention relates to compounds of formula (I), in which $R^5$ represents a —C(O)O$R^9$ group.

In another preferred embodiment the invention relates to compounds of formula (I), in which $R^5$ represents a —C(O)N$R^{10}R^{11}$ group.

In a particularly preferred embodiment the invention relates to compounds of formula (I), in which $R^5$ represents a group selected from a hydrogen atom and cyano.

In another particularly preferred embodiment the invention relates to compounds of formula (I), in which $R^5$ represents a cyano group.

In another particularly preferred embodiment the invention relates to compounds of formula (I), in which $R^5$ represents a hydrogen atom.

In another embodiment the invention relates to compounds of formula (I), in which $R^6$, $R^7$ represent, independently from each other, a group selected from a hydrogen atom, a fluoro atom, a chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from a hydrogen atom, a fluoro atom and a chloro atom.

In another embodiment the invention relates to compounds of formula (I), in which $R^6$ and $R^7$ represent, independently from each other, a group selected from a hydrogen atom and a fluoro atom.

In a particularly preferred embodiment the invention relates to compounds of formula (I), in which $R^6$ represents hydrogen, para-fluoro, or para-chloro, whereby para refers to the point of attachment of $R^2$ to the rest of the molecule, and in which $R^7$ represents a hydrogen atom.

In another particularly preferred embodiment the invention relates to compounds of formula (I), in which $R^6$ represents para-fluoro, whereby para refers to the point of attachment of $R^2$ to the rest of the molecule, and in which $R^7$ represents a hydrogen atom.

In another particularly preferred embodiment the invention relates to compounds of formula (I), in which $R^6$ represents para-fluoro, whereby para refers to the point of attachment of $R^2$ to the rest of the molecule.

In a particularly preferred embodiment the invention relates to compounds of formula (I), in which $R^7$ represents a hydrogen atom.

In another embodiment the invention relates to compounds of formula (I), in which $R^{8a}$, $R^{8b}$ represent, independently from each other, a group selected from hydrogen, a fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^{8a}$, $R^{8b}$ represent, independently from each other, a group selected from hydrogen, a fluoro atom, chloro atom, bromo atom, cyano, methyl-, methoxy-, halomethyl-, fluoromethoxy-.

In another embodiment the invention relates to compounds of formula (I), in which $R^9$ represents a group selected from $C_1$-$C_6$-alkyl-, $C_1$-$C_3$-haloalkyl-, $C_3$-$C_7$-cycloalkyl-, heterocyclyl-, phenyl-, benzyl- and heteroaryl-,
  wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^9$ represents a group selected from $C_1$-$C_3$-alkyl-, halo-$C_1$-$C_3$-alkyl- and benzyl-group, the phenyl group of which is optionally substituted with one or two substituents, identically or differently, selected from the group of halogen, $C_1$-$C_3$-alkyl-, $C_1$-$C_3$-alkoxy-, —NH$_2$, alkylamino-, dialkylamino-.

In another preferred embodiment the invention relates to compounds of formula (I), in which $R^9$ represents a group selected from $C_1$-$C_3$-alkyl-, benzyl- and trifluoromethyl-.

In another preferred embodiment the invention relates to compounds of formula (I), in which $R^9$ represents a group selected from methyl-, ethyl- and trifluoromethyl-.

In another preferred embodiment the invention relates to compounds of formula (I), in which $R^9$ represents a group selected from methyl- and ethyl-.

In another preferred embodiment the invention relates to compounds of formula (I), in which $R^9$ represents a group selected from methyl- and trifluoromethyl-.

In another preferred embodiment the invention relates to compounds of formula (I), in which $R^9$ represents a group selected from ethyl- and trifluoromethyl-.

In another preferred embodiment the invention relates to compounds of formula (I), in which $R^9$ represents a trifluoromethyl- group.

In another embodiment the invention relates to compounds of formula (I), in which $R^{10}$, $R^{11}$ represent, independently from each other, a group selected from a hydrogen atom, $C_1$-$C_6$-alkyl-, $C_3$-$C_7$-cycloalkyl-, heterocyclyl-, phenyl-, benzyl- and heteroaryl-,
wherein said $C_1$-$C_6$-alkyl-, $C_3$-$C_7$-cycloalkyl-, heterocyclyl-, phenyl-, benzyl- or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine.

In a preferred embodiment the invention relates to compounds of formula (I), in which $R^{10}$ and $R^{11}$ represent, independently from each other, a group selected from a hydrogen atom, $C_1$-$C_3$-alkyl- and benzyl-, or $R^{10}$ and $R^{11}$, together with the nitrogen atom they are attached to, form a cyclic amine.

In a preferred embodiment the invention relates to compounds of formula (I), in which $R^{10}$ and $R^{11}$, together with the nitrogen atom they are attached to, form a cyclic amine.

In another preferred embodiment the invention relates to compounds of formula (I), in which $R^{10}$ and $R^{11}$ represent, independently from each other, a group selected from a hydrogen atom and $C_1$-$C_2$-alkyl-.

In another preferred embodiment the invention relates to compounds of formula (I), in which $R^{10}$ and $R^{11}$ represent, independently from each other, a group selected from a hydrogen atom and $C_1$-$C_3$-alkyl-.

In another preferred embodiment the invention relates to compounds of formula (I), in which $R^{10}$ and $R^{11}$ represent, independently from each other, a hydrogen atom or $C_1$-$C_6$-alkyl-.

In a particularly preferred embodiment the invention relates to compounds of formula (I), in which $R^{10}$ and $R^{11}$ represent a hydrogen atom.

In another particularly preferred embodiment the invention relates to compounds of formula (I), in which $R^{10}$ represents a $C_1$-$C_3$-alkyl- group, and $R^{11}$ represents a hydrogen atom.

In another particularly preferred embodiment the invention relates to compounds of formula (I), in which $R^{10}$ represents a $C_1$-$C_2$-alkyl- group, and $R^{11}$ represents a hydrogen atom.

In another particularly preferred embodiment the invention relates to compounds of formula (I), in which $R^{10}$ represents an ethyl- group, and $R^{11}$ represents a hydrogen atom.

In another particularly preferred embodiment the invention relates to compounds of formula (I), in which $R^{10}$ represents a methyl- group, and $R^{11}$ represents a hydrogen atom.

In a preferred embodiment the invention relates to compounds of formula (I), in which $R^{10}$ represents a group selected from hydrogen, $C_1$-$C_3$-alkyl- and benzyl-.

In another preferred embodiment the invention relates to compounds of formula (I), in which $R^{10}$ represents a $C_1$-$C_2$-alkyl- group.

In a particularly preferred embodiment the invention relates to compounds of formula (I), in which $R^{10}$ represents a hydrogen atom.

In another preferred embodiment the invention relates to compounds of formula (I), in which $R^{11}$ represents a group selected from a hydrogen atom and a $C_1$-$C_2$-alkyl- group.

In a particularly preferred embodiment the invention relates to compounds of formula (I), in which $R^{11}$ represents a hydrogen atom.

In another embodiment the invention relates to compounds of formula (I), in which $R^{12}$ represents a group selected from a hydrogen atom, $C_1$-$C_4$-alkyl- and benzyl-.

In a preferred embodiment the invention relates to compounds of formula (I), in which $R^{12}$ represents a group selected from a hydrogen atom and $C_1$-$C_2$-alkyl-.

In another preferred embodiment the invention relates to compounds of formula (I), in which $R^{12}$ represents a group selected from a hydrogen atom and methyl-.

In another preferred embodiment the invention relates to compounds of formula (I), in which $R^{12}$ represents a hydrogen atom.

It is to be understood that the present invention relates to any sub-combination within any embodiment of the present invention of compounds of formula (I), supra.

In another preferred embodiment the invention relates to a specific stereoisomer of compounds of the formula (I) featuring a lower $IC_{50}$ vs CDK9 as compared to other stereoisomers of the respective compound, determined according to Method 1a. described in the Materials and Methods section below.

In another preferred embodiment the invention relates to a specific stereoisomer of compounds of the formula (I) featuring a lower $IC_{50}$ vs CDK9 at high ATP concentration as compared to other stereoisomers of the respective compound, determined according to Method 1b. described in the Materials and Methods section below.

In another preferred embodiment the invention relates to a specific stereoisomer of compounds of the formula (I) featuring a higher selectivity in favor of CDK9 over CDK2 as compared to other stereoisomers of the respective compound, determined according to Methods 1a. (CDK9) and 2a. (CDK2) described in the Materials and Methods section below.

In another preferred embodiment the invention relates to a specific stereoisomer of compounds of the formula (I) featuring a higher selectivity in favor of CDK9 over CDK2 at high ATP concentrations as compared to other stereoisomers of the respective compound, determined according to Methods 1b. (CDK9 High-ATP) and 2b. (CDK2 High-ATP) described in the Materials and Methods section below.

In another preferred embodiment the invention relates to a specific stereoisomer of compounds of the formula (I) featuring a higher anti-proliferative activity in tumor cell lines such as HeLa, HeLa-MaTu-ADR, NCI-H460, DU145, Caco-2, B16F10, A2780 or MOLM-13, as compared to other stereoisomers of the respective compound, determined according to Method 3. described in the Materials and Methods section below.

In another preferred embodiment the invention relates to a specific stereoisomer of compounds of the formula (I) featuring a higher an increased apparent Caco-2 permeability ($P_{app}$ A-B) across Caco-2 cell monolayers, and/or a decreased efflux ratio (efflux ratio=$P_{app}$ B-A/$P_{app}$ A-B) from the basal to apical compartment across Caco-2 cell monolayers, compared to other stereoisomers of the respective compound, determined according to Method 4. described in the Materials and Methods section below.

More particularly still, the present invention covers compounds of formula (I) which are disclosed in the Example section of this text, infra.

Very specially preferred are combinations of two or more of the abovementioned preferred embodiments.

In particular, a preferred subject of the present invention is a compound selected from:

(rac)-[(3-{[5-Fluoro-4-(4-fluoro-1-benzofuran-7-yl)pyrimidin-2-yl]amino}benzyl)(methyl)oxido-λ⁶-sulfanylidene]cyanamide;

[(3-{[5-Fluoro-4-(4-fluoro-1-benzofuran-7-yl)pyrimidin-2-yl]amino}benzyl)(methyl)oxido-λ⁶-sulfanylidene]cyanamide; Enantiomer 1;

[(3-{[5-Fluoro-4-(4-fluoro-1-benzofuran-7-yl)pyrimidin-2-yl]amino}benzyl)(methyl)oxido-λ⁶-sulfanylidene]cyanamide; Enantiomer 2;

(rac)-5-Fluoro-4-(4-fluoro-1-benzofuran-7-yl)-N—{3-[(S-methylsulfonimidoyl)-methyl]phenyl}-pyrimidin-2-amine;

5-Fluoro-4-(4-fluoro-1-benzofuran-7-yl)-N—{3-[(S-methylsulfonimidoyl)-methyl]-phenyl}-pyrimidin-2-amine; Enantiomer 1;

5-Fluoro-4-(4-fluoro-1-benzofuran-7-yl)-N—{3-[(S-methylsulfonimidoyl)-methyl]-phenyl}-pyrimidin-2-amine; Enantiomer 2;

(rac)-[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide;

[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide; Enantiomer 1;

[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide; Enantiomer 2;

(rac)-5-Fluoro-4-(4-fluoro-1-benzofuran-7-yl)-N-{3-fluoro-5-[(S-methylsulfonimidoyl)-methyl]-phenyl}-pyrimidin-2-amine;

5-Fluoro-4-(4-fluoro-1-benzofuran-7-yl)-N—{3-fluoro-5-[(S-methylsulfonimidoyl)-methyl]-phenyl}-pyrimidin-2-amine; Enantiomer 1;

5-Fluoro-4-(4-fluoro-1-benzofuran-7-yl)-N—{3-fluoro-5-[(S-methylsulfonimidoyl)-methyl]-phenyl}-pyrimidin-2-amine; Enantiomer 2;

(rac)-[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide;

[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide; Enantiomer 1;

[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide; Enantiomer 2;

(rac)-5-Fluoro-4-(4-fluoro-1-benzofuran-7-yl)-N—{3-methyl-5-[(S-methylsulfonimidoyl)-methyl]phenyl}pyrimidin-2-amine;

(rac)-{[3-{[5-fluoro-4-(4-fluoro-1-benzofuran-7-yl)pyrimidin-2-yl]amino}-5-(pentafluoro-λ⁶-sulfanyl)benzyl](methyl)oxido-λ⁶-sulfanylidene}cyanamide, and (rac)-5-Fluoro-4-(4-fluoro-1-benzofuran-7-yl)-N-{3-[(S-methylsulfonimidoyl)methyl]-5-(pentafluoro-λ⁶-sulfanyl)phenyl}pyrimidin-2-amine;

and the enantiomers, diastereomers, salts, solvates or salts of solvates thereof.

The above mentioned definitions of radicals which have been detailed in general terms or in preferred ranges also apply to the end products of the formula (I) and, analogously, to the starting materials or intermediates required in each case for the preparation.

The invention further relates to compounds of the formula (6), in which $R^1$, $R^2$, $R^3$ and $R^4$ are as defined for the compounds of formula (I) according to the present invention,

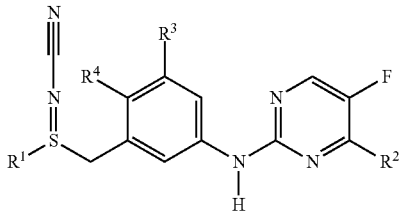

and the enantiomers, diastereomers, salts, solvates or salts of solvates thereof.

The invention further relates to the use of compounds of the formula (6), in which $R^1$, $R^2$, $R^3$ and $R^4$ are as defined for the compounds of formula (I) according to the present invention,

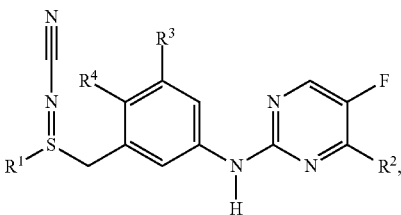

and the salts, solvates or salts of solvates thereof, for the preparation of compounds of the formula (I).

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as the enantiomers, diastereomers, salts, solvates and salts of solvates thereof are used as inhibitors of CDK9. Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as the enantiomers, diastereomers, salts, solvates and salts of solvates thereof selectively inhibit CDK9 in comparison to other cyclin-dependent protein kinases, preferably in comparison to CDK2, in particular at high ATP concentrations. Thus, the compounds according to the general formula (I) as well as pharmaceutically acceptable salts thereof are preferably used as selective inhibitors for CDK9. Compounds of the present invention according to general formula (I) show a significantly stronger CDK9 than CDK2 inhibition, particularly at high ATP concentrations.

In context of the present invention, the $IC_{50}$ value with respect to CDK2 can be determined by the methods described in the method section below. Preferably, it is determined according to Method 2a. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b. ("CDK9/CycT1 high ATP kinase assay") as described in the Materials and Method section below.

In context of the present invention, the $IC_{50}$ value with respect to CDK2 at high ATP concentrations can be determined by the methods described in the method section below. Preferably, it is determined according to Method 2b. ("CDK2/CycE high ATP kinase assay") as described in the Materials and Method section below.

Further, preferred compounds of the present invention according to formula (I) show an improved anti-proliferative activity in tumor cell lines such as HeLa, HeLa-MaTu-ADR, NCI-H460, DU145, Caco-2, B16F10, A2780 or MOLM-13, compared to the CDK9 inhibitors described in the prior art.

In context of the present invention, the anti-proliferative activity in tumor cell lines such as HeLa, HeLa-MaTu-ADR, NCI-H460, DU145, Caco-2, B16F10, A2780 or MOLM-13, is preferably determined according to Method 3. ("Proliferation Assay") as described in the Materials and Method section below.

Further, preferred compounds of the present invention according to formula (I) are characterized by improved pharmacokinetic properties, such as an increased apparent Caco-2 permeability ($P_{app}$ A-B) across Caco-2 cell monolayers, compared to the compounds known from the prior art.

Further, preferred compounds of the present invention according to formula (I) are characterized by improved pharmacokinetic properties, such as a decreased efflux ratio (efflux ratio=$P_{app}$ B-A/$P_{app}$ A-B) from the basal to apical compartment across Caco-2 cell monolayers, compared to the compounds known from the prior art.

In context of the present invention, the apparent Caco-2 permeability values from the basal to apical compartment ($P_{app}$ A-B) or the efflux ratio (defined as the ratio (($P_{app}$ B-A)/($P_{app}$ A-B)) are preferably determined according to Method 4. ("Caco-2 Permeation Assay"), described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, salivary gland cancers, and anal gland adenocarcinomas.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, non-melanoma skin cancer, and mast cell tumors.

Head-and-neck cancers include, but are not limited to laryngeal, hypopharyngeal, nasopharyngeal, oropharyngeal cancer, lip and oral cavity cancer, squamous cell cancer, and oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma, malignant histiocytosis, fibrosarcoma, hemangiosarcoma, hemangiopericytoma, and leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syn-dromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention as a medicament.

A further subject matter of the present invention is the use of the compounds of general formula (I) according to the invention for the treatment and/or prophylaxis of disorders, in particular of the disorders mentioned above.

A further subject matter of the present invention is the use of the compounds of general formula (I) according to the invention for the treatment and/or prophylaxis of hyper-proliferative disorders, virally induced infectious diseases and/or of cardiovascular diseases.

A preferred subject matter of the present invention is the use of the compounds of general formula (I) according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds according to the invention for the use as a medicament.

A further subject matter of the present invention are the compounds according to the invention for the use of treating and/or prophylaxis of the disorders mentioned above.

A further subject matter of the present invention are the compounds according to the invention for the use of treating and/or prophylaxis of hyper-proliferative disorders, virally induced infectious diseases and/or of cardiovascular diseases.

A preferred subject matter of the present invention are the compounds according to the invention for the use of treating and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds according to the invention for the use in a method for the treatment and/or prophylaxis of the disorders mentioned above.

A further subject matter of the present invention are the compounds according to the invention for the use in a method for the treatment and/or prophylaxis of hyper-proliferative disorders, virally induced infectious diseases and/or of cardiovascular diseases.

A preferred subject matter of the present invention are the compounds according to the invention for the use in a method of treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is the use of the compounds according to the invention in the manufacture of a medicament for the treatment and/or prophylaxis of disorders, in particular the disorders mentioned above.

A further subject matter of the present invention is the use of the compounds according to the invention in the manufacture of a medicament for the treatment and/or prophylaxis of hyper-proliferative disorders, virally induced infectious diseases and/or of cardiovascular diseases.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is a method for the treatment and/or prophylaxis of disorders, in particular the disorders mentioned above, using an effective amount of the compounds according to the invention.

A further subject matter of the present invention is a method for the treatment and/or prophylaxis of hyper-proliferative disorders, virally induced infectious diseases and/or of cardiovascular diseases, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias using an effective amount of the compounds according to the invention.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Another aspect of the present invention relates to the use of the pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Another aspect of the present invention relates to pharmaceutical combinations and/or the pharmaceutical compositions according to the invention for the treatment and/or prophylaxis of disorders, in particular of the disorders mentioned above.

Another aspect of the present invention relates to pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art. Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CycT1 Kinase Assay:

CDK9/CycT1-Inhibitory Activity of Compounds of the Present Invention was Quantified Employing the CDK9/CycT1 TR-FRET Assay as Described in the Following Paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 μl of a solution of CDK9/CycT1 in aqueous assay buffer [50 mM Tris/HCl pH 8.0, 10 mM $MgCl_2$, 1.0 mM dithiothreitol, 0.1 mM sodium orthovanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.67 μM=>final conc. in the 5 μl assay volume is 1 μM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 μg/mL. The reaction was stopped by the addition of 5 μl of a solution of TR-FRET detection reagents (0.2 μM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

1b. CDK9/CycT1 High ATP Kinase Assay

CDK9/CycT1-Inhibitory Activity of Compounds of the Present Invention at a High ATP Concentration after Preincubation of Enzyme and Test Compounds was Quantified Employing the CDK9/CycT1 TR-FRET Assay as Described in the Following Paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 μl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 3.3 mM=>final conc. in the 5 μl assay volume is 2 mM) and substrate (1.67 μM=>final conc. in the 5 μl assay volume is 1 μM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 μg/mL. The reaction was stopped by the addition of 5 μl of a solution of TR-FRET detection reagents (0.2 μM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2a. CDK2/CycE kinase assay:

CDK2/CycE-Inhibitory Activity of Compounds of the Present Invention was Quantified Employing the CDK2/CycE TR-FRET Assay as Described in the Following Paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 yl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 yl of a solution of adenosine-tri-phosphate (ATP, 16.7 μM=>final conc. in the 5 yl assay volume is 10 μM) and substrate (1.25 μM=>final conc. in the 5 yl assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 yl of a solution of TR-FRET detection reagents (0.2 μM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2b. CDK2/CycE High ATP Kinase Assay:

CDK2/CycE-Inhibitory Activity of Compounds of the Present Invention at 2 mM Adenosine-Tri-Phosphate (ATP) was Quantified Employing the CDK2/CycE TR-FRET (TR-FRET=Time Resolved Fluorescence Energy Transfer) Assay as Described in the Following Paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 yl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 yl of a solution ATP (3.33 mM=>final conc. in the 5 yl assay volume is 2 mM) and substrate (1.25 M=>final conc. in the 5 yl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 15 ng/ml. The reaction was stopped by the addition of 5 yl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The $IC_{50}$ values (inhibitory concentration at 50% of maximal effect) were determined by means of a 4 parameter fit.

Non-adherent MOLM-13 human acute myeloid leukemia cells (DSMZ ACC 554) were seeded at a density of 5,000 cells/well in a 96-well multititer plate in 100 μL of growth medium supplemented 10% fetal calf serum. After 24 hours, cell viability of one plate (zero-point plate) was determined with the Cell Titre-Glo Luminescent Cell Viability Assay (Promega), while 50 μL of test compound containing medium was added to the wells of the other plates (final concentrations in the range of 0.001-10 μM and DMSO controls; the final concentration of the solvent dimethyl sulfoxide was 0.5%). Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

4. Caco-2 Permeation Assay:

Caco-2 cells (purchased from DSMZ Braunschweig, Germany) were seeded at a density of $4.5 \times 10^4$ cells per well on 24 well insert plates, 0.4 μm pore size, and grown for 15 days in DMEM medium supplemented with 10% fetal bovine serum, 1% GlutaMAX (100×, GIBCO), 100 U/mL penicillin, 100 μg/mL streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by a FCS-free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 μM in transport buffer. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$Papp=(Vr/Po)(1/S)(P2/t)$

Where Vr is the volume of medium in the receiver chamber, Po is the measured peak area or height of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B-A by the Papp A-B. In addition the compound recovery was calculated.

PREPARATIVE EXAMPLES

General Syntheses of Compounds of Formula (I)

The syntheses of 4-(benzofuran-7-yl)-substituted 5-fluoro-pyrimidine derivatives of formula (I) according to the present invention, and subsets thereof, such as e.g. compounds of formulae (7), (8) and (10), can be carried out according to schemes 1 and 2 below.

In addition to said routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, interconversion of any of the substituents $R^1$, $R^2$, $R^3$, $R^4$ and/or $R^5$ can be achieved before and/or after the exemplified transformations. These modifications can be such as the introduction of protective groups, cleavage of protective groups, reduction or oxidation of functional groups, halogenation, metallation, metal catalysed coupling reactions, substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, $4^{th}$ edition, Wiley 2006). Specific examples are described in the subsequent paragraphs. Further, it is possible that two or more successive steps may be performed without work-up being performed between said steps, e.g. a "one-pot" reaction, as it is well-known to a person skilled in the art.

The geometry of the sulfoximine moiety renders the compounds of the general formula (I) chiral. Separation of racemic sulfoximines into their enantiomers can be achieved by methods known to the person skilled in the art, preferably by means of preparative HPLC on chiral stationary phase.

In the first step, 2,4-dichloro-5-fluoropyrimidine (1; CAS-No. 2927-71-1) is reacted with a boronic acid derivative $R^2$—$B(OR)_2$ of formula (2), in which $R^2$ is as defined for the compound of general formula (I), to give a compound of formula (3). The boronic acid derivative (2) may preferably be a boronic acid (R═—H), or, alternatively, an ester of said boronic acid, e.g. its isopropyl ester (R═—CH($CH_3$)$_2$), or a cyclic ester derived from pinacol in which the —B(OR)$_2$ forms a -4,4,5,5-tetramethyl-1,3,2-dioxaborolane (R—R═—C(CH$_3$)$_2$—C(CH$_3$)$_2$—). Boronic acids and their esters are commercially available and well-known to the person skilled in the art; see e.g. D. G. Hall, Boronic Acids, 2005 WILEY-VCH Verlag GmbH & Co. KGaA, Weinheim, ISBN 3-527-30991-8 and references cited therein.

The coupling reaction is catalyzed by Pd catalysts, e.g. by Pd(0) catalysts such as tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts such as dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl$_2$]; preferably by 1,1'-bis(diphenylphosphino)ferrocenedichloropalladium(II)-dichlormethane.

The reaction is preferably carried out in a mixture of a solvent such as 1,2-dimethoxyethane, dioxane, DMF, THF, or isopropanol with water and in the presence of a base such as aqueous potassium carbonate, aqueous sodium bicarbonate or potassium phosphate.

A synthetic route to N-cyanosulfoximines of formula (7) is shown in Scheme 1.

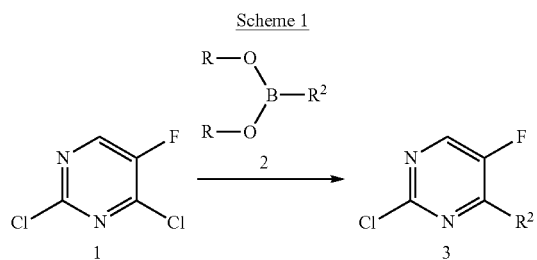

Scheme 1

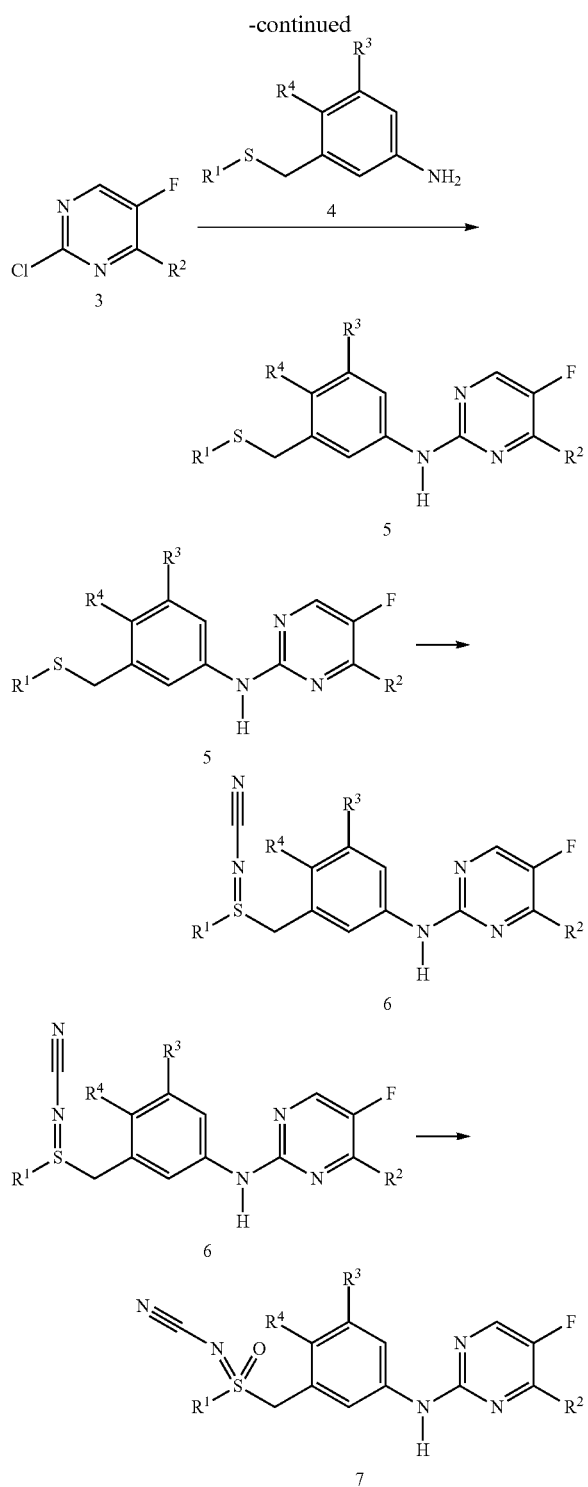

In the following step, a compound of formula (3) is reacted in a coupling reaction with an aniline of formula (4), in which R¹, R³ and R⁴ are as defined for the general formula (I), to give a compound of formula (5).

Said coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the use of suitable palladium precatalysts based upon biarylmonophosphines which are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tetrahedron Lett. 2009, 50, 3672). Most preferred is the herein described use of chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-tri-isopropylbiphenyl and potassium phosphate in a mixture of toluene and NMP (1-methylpyrrolidin-2-one) as solvent. The reactions are preferably run under argon for 3-48 hours at an elevated temperature, for example 130° C., in a microwave oven or in an oil bath.

Another preferred variation is the use of tris(dibenzylideneacetone)dipalladium(0), (9,9-dimethyl-9H-xanthene-4,5-diyl)bis(diphenylphosphane) and and cesium carbonate in dioxane, the reactions being preferably run under argon for 3-48 hours at an elevated temperature, for example 130° C., in a microwave oven or in an oil bath.

Alternatively, this coupling reaction can be carried out in an alcohol such as 1-butanol or in an inert solvent such as DMF, THF, DME, dioxane or mixtures of such solvents in the presence of an acid such as hydrogen chloride or 4-methylbenzenesulfonic acid. Preferably, the reaction is carried out at an elevated temperature, for example 140° C.

Anilines of formula (4) are commercially available in certain cases, or can be prepared by methods known to the person skilled in the art, e.g. from the corresponding 3-aminobenzylic alcohols via conversion of the hydroxy group contained therein into a suitable leaving group, such as chloro or bromo, followed by nucleophilic displacement with a thiol of the general formula R¹—SH, in which R¹ is defined as defined for the compound of general formula (I). If needed, the amino group present in said 3-aminobenzylic alcohols can be protected by a suitable protecting group. Protecting groups for amino groups present in analogues and methods for their introduction and removal are well known to the person skilled in the art, see e.g. T. W. Greene and P. G. M. Wuts in: Protective Groups in Organic Synthesis, $4^{th}$ edition, Wiley (2006).

Thiols of formula R¹—SH are known to the person skilled in the art and are commercially available in considerable variety.

In the third step, a compound of formula (5) is reacted with cyanamide as a nitrogen source to give the corresponding N-cyanosulfilimine of formula (6). The reaction can be carried out using NBS and potassium tert-butoxide in methanol at room temperature (see for example: a) C. Bolm et al, Org. Lett. 2007, 9, 3809). Instead of NBS, iodine or iodobenzene diacetate (PhI(OAc)₂) can be employed (see for example: a) C. Bolm et al, Org. Lett. 2007, 9, 3809; b) C. Bolm et al, Bioorg. Med. Chem. Lett. 2011, 21, 4888; c) J. M. Babcock, US 2009/0023782). Preferred is the herein described use of iodobenzene diacetate.

Finally, the N-cyanosulfilimine of formula (6) is oxidized to the corresponding N-cyanosulfoximine of formula (7). The reaction can be carried out using mCPBA and potassium carbonate in ethanol at room temperature (see for example: a) C. Bolm et al, Org. Lett. 2007, 9, 3809). Alternatively, other oxidazing agents such as potassium peroxomonosulfate or sodium periodate/ruthenium trichloride can be employed (see for example: a) J. M. Babcock, US 2009/0023782). Preferred is the herein described use of potassium permanganate in acetone.

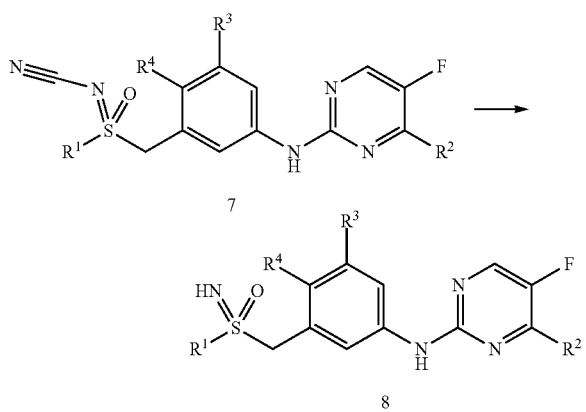

N-cyanosulfoximines of formula (7) can be converted to the corresponding N-unprotected sulfoximines of formula (8). The reaction is preferably carried out using trifluoroacetic anhydride (TFAA) in DCM followed by reaction with potassium carbonate in methanol (see for example: a) C. Bolm et al, Org. Lett. 2007, 9, 3809).

An alternative synthetic access to compounds of the formula (I), e.g. to sulfoximines of formula (8) is shown in Scheme 2.

In a first step, a compound of formula (3) can be reacted with an aniline of formula (9) to give the corresponding cross-coupling product of formula (10). The compounds of formula (10) can be prepared by Palladium-catalyzed C—N cross-coupling reactions (for a review on C—N cross-coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004). Anilines of the formula (9) and methods of their preparation are e.g. described in WO 2014/076028.

Said Palladium-catalyzed C—N cross-coupling reactions can be catalysed by suitable palladium precatalysts based upon biarylmonophosphines that are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tetrahedron Lett. 2009, 50, 3672), Suitably, chloro(2-dicyclohexylphosphino-2',4',6'-tri-iso-propyl-1,1'-biphenyl)[2-(2-aminoethyl)phenyl]palladium(II) methyl-tert-butylether adduct and 2-dicyclohexylphosphino-2',4',6'-triisopropylbiphenyl as precatalyst and ligand, potassium phosphate as a base, and a mixture in toluene and 1-methylpyrrolidin-2-one as a solvent can be used.

Scheme 2

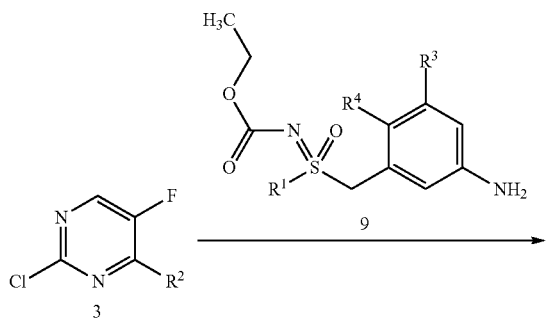

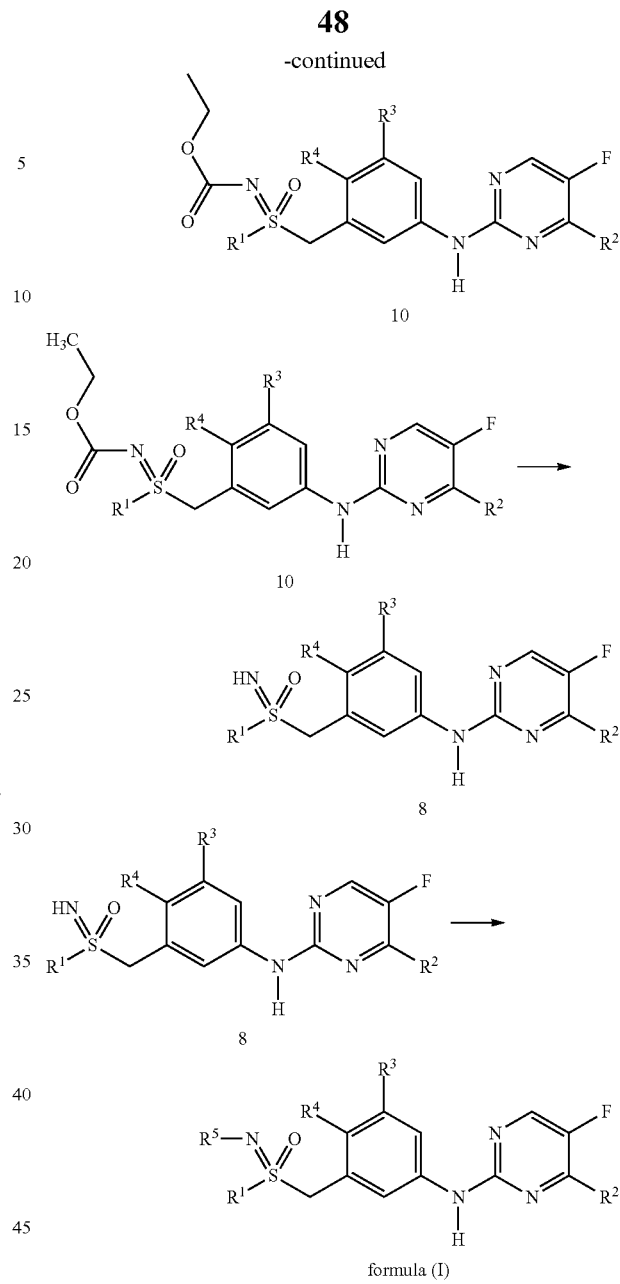

Deprotection of compounds of formula (10) can e.g. be performed using sodium ethoxide in ethanol at 60° C., to yield the corresponding N-unprotected sulfoximines of formula (8).

N-unprotected sulfoximines of formula (8) can be reacted to give further N-functionalized derivatives of formula (I). There are multiple methods for the preparation of N-functionalized sulfoximines by functionalization of the nitrogen of the sulfoximine group:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

Reaction with bromocyane: see for example: a) D. T. Sauer et al, Inorganic Chemistry 1972, 11, 238; b) C. Bolm et al, Org. Lett. 2007, 9, 2951; c) U. Lücking et al, WO 2011/29537.

Preparation of Compounds:

Abbreviations Used in the Description of the Chemistry and in the Examples that Follow are:

$CDCl_3$ (deuterated chloroform); cHex (cyclohexane); d (doublet); DCM (dichloromethane); DIPEA (di-iso-propylethylamine); DME (1,2-dimethoxyethane); DMF (dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); NBS (N-bromosuccinimide), NMP (1-methylpyrrolidin-2-one), NMR (nuclear magnetic resonance); p (pentet); $Pd(dppf)Cl_2$ ([1,1'-bis(diphenylphosphino)ferrocene]dichloro palladium(II) complex with dichloromethane); iPrOH (iso-propanol); q (quartet); RT (room temperature); s (singlet); sat. aq. (saturated aqueous); $SiO_2$ (silica gel); TFA (trifluoroacetic acid); TFAA (trifluoroacetic anhydride), THF (tetrahydrofuran); tr (triplet).

The IUPAC names of the examples were generated using the program 'ACD/Name batch version 12.01' from ACD LABS.

EXAMPLE 1

(rac)-[(3-{[5-Fluoro-4-(4-fluoro-1-benzofuran-7-yl)pyrimidin-2-yl]amino}benzyl)(methyl)oxido-λ⁶-sulfanylidene]cyanamide

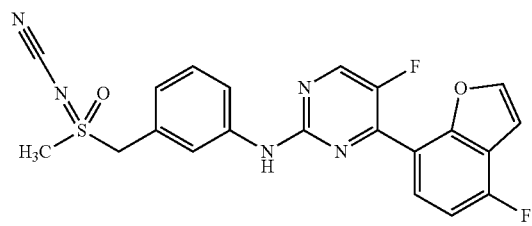 [SMILES: CS(=O)(Cc1cccc(Nc2ncc(F)c(-c3ccc(F)c4ccoc34)n2)c1)=NC#N]

Preparation of Intermediate 1.1

1-[(Methylsulfanyl)methyl]-3-nitrobenzene

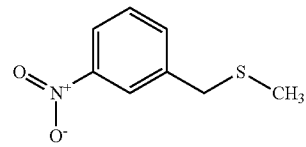

Sodium methanethiolate (13.5 g; 192 mmol) was added in two portions to a stirred solution of 1-(chloromethyl)-3-nitrobenzene (30.0 g; 175 mmol; Aldrich Chemical Company Inc.) in ethanol (360 mL) at −15° C. The cold bath was removed and the batch was stirred at room temperature for 3 hours. The batch was diluted with saturated aqueous sodium chloride solution and extracted twice with ethyl acetate. The combined organic layers were washed with water, dried (sodium sulfate), filtered and concentrated to give the desired product (32.2 g) that was used without further purification.

$^1$H NMR (400 MHz, $CDCl_3$) δ=8.18 (m, 1H), 8.11 (m, 1H), 7.66 (m, 1H), 7.50 (m, 1H), 3.75 (s, 2H), 2.01 (s, 3H).

Preparation of Intermediate 1.2

3-[(Methylsulfanyl)methyl]aniline

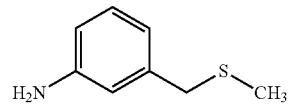

Titanium(III)chloride solution (approx. 15%) in approx. 10% aqueous hydrochloric acid (389 mL; Merck Schuchardt OHG) was added to a stirred solution of 1-[(methylsulfanyl)methyl]-3-nitrobenzene (10.5 g; 57.3 mmol; Intermediate 1.1) in THF (680 mL) at room temperature and the batch was stirred for 45 hours. By adding 1N sodium hydroxide solution the pH value of the reaction mixture was raised to 7 before the batch was extracted twice with ethyl acetate. The combined organic layers were washed with brine, dried over sodium sulfate and concentrated. The residue was purified by column chromatography on silica gel (hexanes/ethyl acetate) to give the desired product (6.56 g; 40.67 mmol).

$^1$H NMR (400 MHz, DMSO-d6) δ=6.93 (t, 1H), 6.50 (t, 1H), 6.46-6.39 (m, 2H), 5.01 (s, 2H), 3.52 (s, 2H), 1.95 (s, 3H).

Preparation of Intermediate 1.3

2-Chloro-5-fluoro-4-(4-fluoro-1-benzofuran-7-yl)pyrimidine

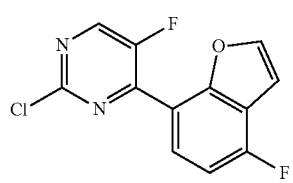 [SMILES: Fc1cnc(Cl)nc1-c1ccc(F)c2ccoc12]

A mixture of 2,4-dichloro-5-fluoropyrimidine (818 mg; 4.90 mmol; Aldrich Chemical Company Inc.), (4-fluoro-1- benzofuran-7-yl)boronic acid (1 g; 5.39 mmol; ABCR GmbH & CO. KG) and 1,1'-bis(diphenylphosphino)ferrocenedichloropalladium(II)-dichlormethane (400.2 mg; 0.49 mmol) and 2 M aqueous solution of potassium carbonate (7.35 mL) in 1,2-dimethoxyethane (25.4 mL) was degassed using argon. The batch was stirred under an atmosphere of argon for 90 minutes at ambient temperature. The batch was diluted with ethyl acetate and washed with brine. The organic layer was dried over sodium sulfate, filtered and concentrated. The residue was purified by column chromatography on silica gel (hexanes/ethyl acetate) to give the desired product (834 mg; 3.13 mmol).

$^1$H NMR (400 MHz, DMSO-$d_6$) δ=9.06 (d, 1H), 8.21 (d, 1H), 7.78 (dd, 1H), 7.38-7.32 (m, 1H), 7.25 (d, 1H).

Preparation of Intermediate 1.4

5-Fluoro-4-(4-fluoro-1-benzofuran-7-yl)-N-{3-[(methylsulfanyl)methyl]phenyl}pyrimidin-2-amine

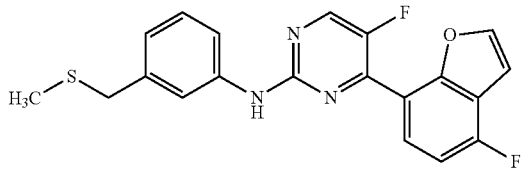 [SMILES: CSCc1cccc(Nc2ncc(F)c(-c3ccc(F)c4ccoc34)n2)c1]

A mixture of 2-chloro-5-fluoro-4-(4-fluoro-1-benzofuran-7-yl)pyrimidine (517 mg; 1.94 mmol; intermediate 1.3), 3-[(methylsulfanyl)methyl]aniline (625 mg; 3.88 mmol), chloro(2-dicyclohexylphosphino-2',4',6'-tri-iso-propyl-1,1'-biphenyl)[2-(2-aminoethyl)phenyl]palladium(II) methyl-tert-butylether adduct (120 mg; 0.145 mmol; ABCR GmbH & CO. KG) and 2-(dicyclohexylphosphino)-2',4',6'-triisopropylbiphenyl (70 mg; 0.145 mmol; Aldrich Chemical Company Inc.) and potassium phosphate (2.06 g; 9.69 mmol) in toluene (43.9 ml) and NMP (3.4 mL) was stirred at 130° C. for 3 hours. After cooling, the batch was diluted with ethyl acetate and washed with aqueous sodium chloride solution. The organic layer was filtered using a Whatman filter and concentrated. The residue was purified by column chromatography on silica gel (hexane/ethyl acetate 2:1) to give the title compound (523 mg; 1.35 mmol).

$^1$H NMR (400 MHz, DMSO-$d_6$) δ=9.85 (s, 1H), 8.71 (d, 1H), 8.20 (d, 1H), 7.81 (t, 1H), 7.77 (dd, 1H), 7.67-7.61 (m, 1H), 7.33 (dd, 1H), 7.25-7.18 (m, 2H), 6.89 (d, 1H), 3.64 (s, 2H), 1.94 (s, 3H).

Preparation of Intermediate 1.5

(rac)-[(3-{[5-Fluoro-4-(4-fluoro-1-benzofuran-7-yl)pyrimidin-2-yl]amino}benzyl)(methyl)-$\lambda^4$-sulfanylidene]-cyanamide

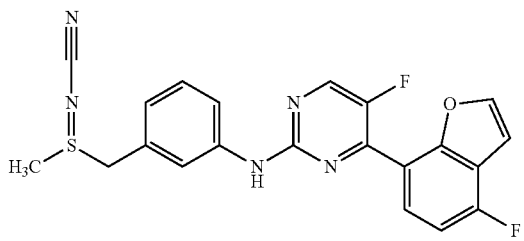 [SMILES: CS(Cc1cccc(Nc2ncc(F)c(-c3ccc(F)c4ccoc34)n2)c1)=NC#N]

Iodobenzene diacetate (517 mg; 1.57 mmol) was added to a stirred solution of 5-fluoro-4-(4-fluoro-1-benzofuran-7-yl)-N-{3-[(methylsulfanyl)methyl]phenyl}pyrimidin-2-amine (590 mg; 1.43 mmol; intermediate 1.4) and cyanamide (121 mg; 2.86 mmol) in DCM (16.3 mL) at 0° C. The batch was stirred for 2.5 hours at this temperature before it was purified by column chromatography on silica gel (hexanes/ethyl acetate) to give the title compound (585 mg; 1.38 mmol).

$^1$H NMR (400 MHz, DMSO-$d_6$) δ=10.02 (s, 1H), 8.72 (d, 1H), 8.21 (d, 1H), 7.87 (s, 1H), 7.83-7.76 (m, 2H), 7.38-7.30 (m, 2H), 7.23 (d, 1H), 7.01 (d, 1H), 4.50-4.21 (m, 2H), 2.84 (s, 3H).

Preparation of End Product:

Potassium permanganate (368 mg; 2.28 mmol) was added to a stirred solution of (rac)-[(3-{[5-Fluoro-4-(4-fluoro-1-benzofuran-7-yl)pyrimidin-2-yl]amino}benzyl)(methyl)-2$^4$-sulfanylidene]-cyanamide (483 mg; 1.14 mmol; intermediate 1.5) in acetone (24.4 mL) at RT. The batch was stirred at 50° C. for one hour. The batch was concentrated and the residue was purified by column chromatography on silica gel (hexanes/ethyl acetate) to give the desired product (267 mg; 0.59 mmol).

$^1$H NMR (400 MHz, DMSO-$d_6$) δ=10.03 (s, 1H), 8.72 (d, 1H), 8.20 (d, 1H), 7.91 (t, 1H), 7.85 (dd, 1H), 7.78 (dd, 1H), 7.40-7.29 (m, 2H), 7.23 (d, 1H), 7.07 (d, 1H), 5.00-4.88 (m, 2H), 3.35 (s, 3H).

EXAMPLES 2 AND 3

Enantiomers of [(3-{[5-Fluoro-4-(4-fluoro-1-benzofuran-7-yl)pyrimidin-2-yl]amino}benzyl)(methyl)oxido-$\lambda^6$-sulfanylidene]cyanamide

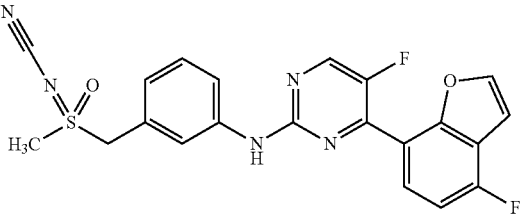 [SMILES: CS(=O)(Cc1cccc(Nc2ncc(F)c(-c3ccc(F)c4ccoc34)n2)c1)=NC#N]

(rac)-[(3-{[5-Fluoro-4-(4-fluoro-1-benzofuran-7-yl)pyrimidin-2-yl]amino}benzyl)(methyl)oxido-$\lambda^6$-sulfanylidene]cyanamide (219 mg) was separated into the enantiomers by chiral preparative HPLC.

| System: | Agilent: Prep 1200, 2xPrep Pump, DLA, MWD, Prep FC |
|---|---|
| Column: | Chiralpak IC 5 μm 250 × 30 mm |
| Solvent: | ethyl acetate/hexanes 50:50 (v/v) |
| Flow: | 40 mL/min |
| Temperature: | 25° C. |
| Solution: | 219 mg/4 mL ethyl acetate |
| Injection: | 8 × 0.5 mL |
| Detection: | UV 280 nm |

| | Retention time in min | Amount | purity in % |
|---|---|---|---|
| Example 2 Enantiomer 1 | 7.4-8.3 | 88 mg | 99 |
| Example 3 Enantiomer 2 | 10.6-11.9 | 91 mg | 99 |

EXAMPLE 4

(rac)-5-Fluoro-4-(4-fluoro-1-benzofuran-7-yl)-N-{3-[(S-methylsulfonimidoyl)-methyl]phenyl}-pyrimidin-2-amine

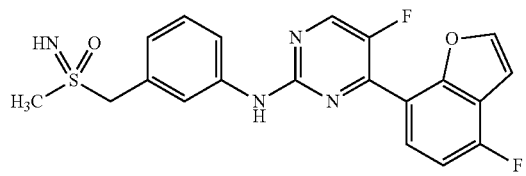 [SMILES: CS(=N)(=O)Cc1cccc(Nc2ncc(F)c(-c3ccc(F)c4ccoc34)n2)c1]

To a stirred solution of (rac)-[(3-{[5-Fluoro-4-(4-fluoro-1-benzofuran-7-yl)pyrimidin-2-yl]amino}-benzyl)(methyl)oxido-$\lambda^6$-sulfanylidene]cyanamide (360 mg; 0.81 mmol; example 1) in DCM (37 mL) at 0° C., TFAA (0.344 mL; 2.43 mmol) was added. The mixture was allowed to react at RT for 2 hours. The reaction mixture was concentrated, re-dissolved in MeOH (5.9 mL) and treated with potassium carbonate (560 mg; 4.05 mmol). The mixture was allowed to react at RT for 18 hours. The reaction mixture was diluted with ethyl acetate and THF and washed with saturated aqueous sodium chloride solution. The organic layer was filtered using a Whatman filter and concentrated. The residue was purified by column chromatography on silica gel (ethyl acetate/MeOH) to give the title compound (152 mg; 0.37 mmol).

$^1$H NMR (400 MHz, DMSO-$d_6$) δ=9.91 (s, 1H), 8.71 (d, 1H), 8.21 (d, 1H), 7.84 (s, 1H), 7.81-7.72 (m, 2H), 7.37-7.26 (m, 2H), 7.23 (d, 1H), 7.02 (d, 1H), 4.37-4.24 (m, 2H), 3.53 (s, 1H), 2.77 (s, 3H).

EXAMPLES 5 AND 6

Enantiomers of 5-Fluoro-4-(4-fluoro-1-benzofuran-7-yl)-N-{3-[(S-methylsulfonimidoyl)-methyl]-phenyl}-pyrimidin-2-amine

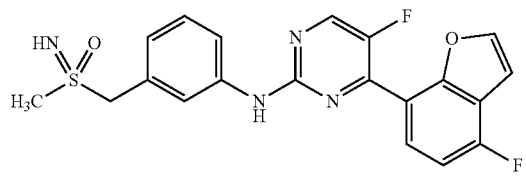 [SMILES: CS(=N)(=O)Cc1cccc(Nc2ncc(F)c(-c3ccc(F)c4ccoc34)n2)c1]

(rac)-5-Fluoro-4-(4-fluoro-1-benzofuran-7-yl)-N-{3-[(S-methylsulfonimidoyl)-methyl]-phenyl}-pyrimidin-2-amine (147 mg) was separated into the enantiomers by chiral preparative HPLC.

| System: | Agilent: Prep 1200, 2xPrep Pump, DLA, MWD, Prep FC |
|---|---|
| Column: | Chiralpak ID 5 μm 250 × 30 mm |
| Solvent: | hexane/ethanol/diethylamine 70:30:0.1 (v/v/v) |
| Flow: | 45 mL/min |
| Temperature: | RT |
| Solution: | 147 mg/2.1 mL DCM |
| Injection: | 3 × 0.7 mL |
| Detection: | UV 280 nm |

| | Retention time in min | Amount | purity in % |
|---|---|---|---|
| Example 5 Enantiomer 1 | 18.2-21.1 min | 50 mg | 97.9 |
| Example 6 Enantiomer 2 | 21.1-25.7 min | 60 mg | 98.5 |

EXAMPLE 7

(rac)-[(3-Fluoro-5-{[5-fluoro-4-(4-fluoro-1-benzofuran-7-yl)pyrimidin-2-yl]amino}benzyl)(methyl)oxido-$\lambda^6$-sulfanylidene]cyanamide

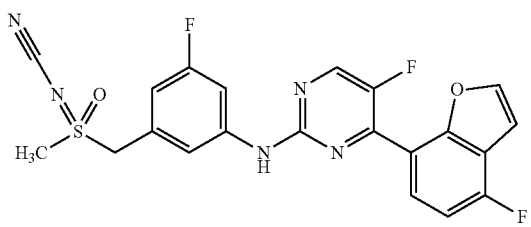 [SMILES: CS(=O)(Cc1cc(F)cc(Nc2ncc(F)c(-c3ccc(F)c4ccoc34)n2)c1)=NC#N]

Preparation of Intermediate 7.1

1-Fluoro-3-[(methylsulfanyl)methyl]-5-nitrobenzene

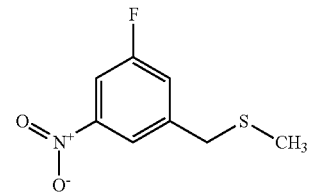

Intermediate 7.1 was prepared under similar conditions as described in the preparation of Intermediate 1.1 using 1-(chloromethyl)-3-fluoro-5-nitrobenzene (Hansa Fine Chemicals GmbH, Germany, CAS #1214344-25-8).

$^1$H NMR (400 MHz, DMSO-$d_6$) δ=8.08 (s, 1H), 7.98 (dt, 1H), 7.70 (dt, 1H), 3.86 (s, 2H), 1.97 (s, 3H).

Preparation of Intermediate 7.2

3-Fluoro-5-[(methylsulfanyl)methyl]aniline

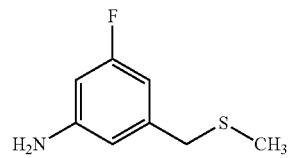

Intermediate 7.2 was prepared under similar conditions as described in the preparation of Intermediate 1.2 using 1-fluoro-3-[(methylsulfanyl)methyl]-5-nitrobenzene (Intermediate 7.1).

¹H NMR (400 MHz, DMSO-d₆) δ=6.32 (t, 1H), 6.24-6.15 (m, 2H), 5.38 (s, 2H), 3.52 (s, 2H), 1.97-1.92 (m, 3H).

Preparation of Intermediate 7.3

5-Fluoro-4-(4-fluoro-1-benzofuran-7-yl)-N-{3-fluoro-5-[(methylsulfanyl)methyl]phenyl}pyrimidin-2-amine

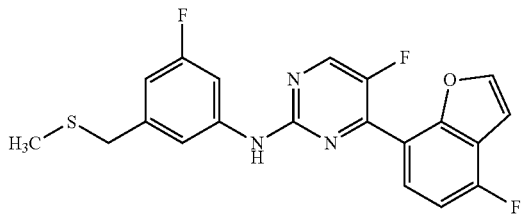 [SMILES: CSCc1cc(F)cc(Nc2ncc(F)c(-c3ccc(F)c4ccoc34)n2)c1]

Intermediate 7.3 was prepared under similar conditions as described in the preparation of Intermediate 1.4 using 2-chloro-5-fluoro-4-(4-fluoro-1-benzofuran-7-yl)pyrimidine (1 g; 3.75 mmol; Intermediate 1.3) and 3-fluoro-5-[(methylsulfanyl)methyl]aniline (1.14 g; 6.56 mmol; intermediate 7.2). The residue was purified by column chromatography on silica gel (hexanes/ethyl acetate) to give the title compound (1.19 g; 2.96 mmol).
¹H NMR (400 MHz, DMSO-d₆) δ=10.10 (s, 1H), 8.76 (d, 1H), 8.18 (d, 1H), 7.81-7.71 (m, 2H), 7.52 (s, 1H), 7.34 (dd, 1H), 7.24 (d, 1H), 6.75-6.69 (m, 1H), 3.64 (s, 2H), 1.96 (s, 3H).

Preparation of Intermediate 7.4

(rac)-[(3-Fluoro-5-{[5-fluoro-4-(4-fluoro-1-benzofuran-7-yl)pyrimidin-2-yl]amino}-benzyl)(methyl)-λ⁴-sulfanylidene]cyanamide

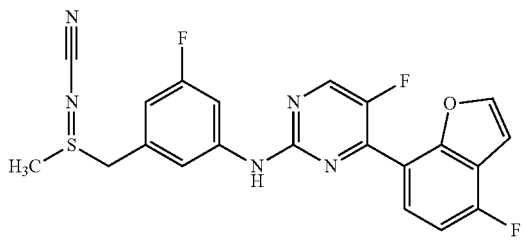 [SMILES: CS(Cc1cc(F)cc(Nc2ncc(F)c(-c3ccc(F)c4ccoc34)n2)c1)=NC#N]

Intermediate 7.4 was prepared under similar conditions as described in the preparation of Intermediate 1.5 using 5-fluoro-4-(4-fluoro-1-benzofuran-7-yl)-N-{3-fluoro-5-[(methylsulfanyl)methyl]-phenyl}-pyrimidin-2-amine (Intermediate 7.3). The batch was purified by column chromatography on silica gel (DCM/MeOH) to give the title compound (1.69 g; 3.71 mmol).
¹H NMR (400 MHz, DMSO-d₆) δ=10.29 (s, 1H), 8.78 (d, 1H), 8.19 (d, 1H), 7.93 (dt, 1H), 7.80 (dd, 1H), 7.57 (s, 1H), 7.40-7.31 (m, 1H), 7.24 (d, 1H), 6.84 (dd, 1H), 4.50-4.21 (m, 2H), 2.85 (s, 3H).

Preparation of End Product:

Example 7 was prepared under similar conditions as described in the preparation of Example 1 using (rac)-[(3-fluoro-5-{[5-fluoro-4-(4-fluoro-1-benzofuran-7-yl)pyrimidin-2-yl]amino}benzyl)(methyl)-λ⁴-sulfanylidene]cyanamide (1.68 g; 3.69 mmol; Intermediate 7.4). The batch was purified by column chromatography on silica gel (hexanes/ethyl acetate) to give the title compound (1.01 g; 2.07 mmol).
¹H NMR (400 MHz, DMSO-d₆) δ=10.30 (s, 1H), 8.78 (d, 1H), 8.18 (d, 1H), 7.99 (dt, 1H), 7.80 (dd, 1H), 7.62 (s, 1H), 7.34 (dd, 1H), 7.24 (d, 1H), 6.92-6.87 (m, 1H), 5.04-4.93 (m, 2H), 3.39 (s, 3H).

EXAMPLES 8 AND 9

Enantiomers of [(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide

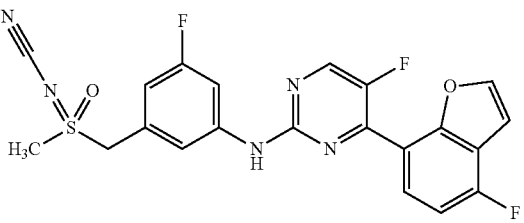 [SMILES: CS(=O)(Cc1cc(F)cc(Nc2ncc(F)c(-c3ccc(F)c4ccoc34)n2)c1)=NC#N]

(rac)-[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide (162 mg) was separated into the enantiomers by chiral preparative HPLC.

| | |
|---|---|
| System: | Agilent: Prep 1200, 2xPrep Pump, DLA, MWD, Prep FC |
| Column: | Chiralpak ID 5 µm 250 × 20 mm |
| Solvent: | hexane/2-propanol/diethylamine 70:30:0.1 (v/v/v) |
| Flow: | 30 mL/min |
| Temperature: | RT |
| Solution: | 162 mg/2.5 mL DMF/DCM |
| Injection: | 5 × 0.5 mL |
| Detection: | UV 280 nm |

| | Retention time in min | Amount | purity in % |
|---|---|---|---|
| Example 8 Enantiomer 1 | 16.9-24.2 | 55 mg | 98.9 |
| Example 9 Enantiomer 2 | 25.2-32.6 | 45 mg | 95.2 |

EXAMPLE 10

(rac)-5-Fluoro-4-(4-fluoro-1-benzofuran-7-yl)-N-{3-fluoro-5-[(S-methylsulfonimidoyl)-methyl]-phenyl}-pyrimidin-2-amine

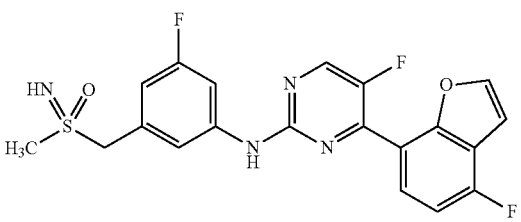 [SMILES: CS(=N)(=O)Cc1cc(F)cc(Nc2ncc(F)c(-c3ccc(F)c4ccoc34)n2)c1]

Example 10 was prepared under similar conditions as described in the preparation of Example 4 using (rac)-[(3- fluoro-5-{[5-fluoro-4-(4-fluoro-1-benzofuran-7-yl)pyrimidin-2-yl]amino}benzyl)(methyl)-oxido-λ⁶-sulfanylidene]cyanamide (784 mg; 1.61 mmol; Example 7). The batch was purified by column chromatography on silica gel (ethyl acetate/MeOH) to give the title compound (272 mg; 0.62 mmol).

¹H NMR (400 MHz, DMSO-d₆) δ=10.16 (s, 1H), 8.76 (d, 1H), 8.19 (d, 1H), 7.86 (dt, 1H), 7.79 (dd, 1H), 7.55 (s, 1H), 7.37-7.30 (m, 1H), 7.24 (d, 1H), 6.86 (d, 1H), 4.38-4.27 (m, 2H), 3.65 (s, 1H), 2.80 (s, 3H).

EXAMPLES 11 AND 12

Enantiomers of 5-Fluoro-4-(4-fluoro-1-benzofuran-7-yl)-N-{3-fluoro-5-[(S-methylsulfonimidoyl)-methyl]-phenyl}-pyrimidin-2-amine

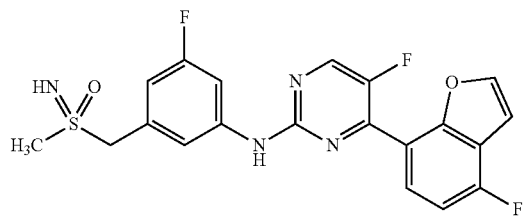 [SMILES: CS(=N)(=O)Cc1cc(F)cc(Nc2ncc(F)c(-c3ccc(F)c4ccoc34)n2)c1]

(rac)-5-Fluoro-4-(4-fluoro-1-benzofuran-7-yl)-N-{3-fluoro-5-[(S-methylsulfonimidoyl)-methyl]-phenyl}-pyrimidin-2-amine (129 mg) was separated into the enantiomers by chiral preparative HPLC.

| System: | Agilent: Prep 1200, 2xPrep Pump, DLA, MWD, Gilson: Liquid Handler 215 |
|---|---|
| Column: | Chiralpak ID 5 μm 250 × 30 mm |
| Solvent: | hexane/ethanol 70:30 (v/v) |
| Flow: | 40 mL/min |
| Temperature: | RT |
| Solution: | 129 mg/9.5 mL DCM/MeOH |
| Injection: | 5 × 1.9 mL |
| Detection: | UV 280 nm |

| | Retention time in min | Amount | purity in % |
|---|---|---|---|
| Example 11 Enantiomer 1 | 14.5-16.2 | 55 mg | 99 |
| Example 12 Enantiomer 2 | 16.2-19.0 | 55 mg | 95.6 |

EXAMPLE 13

(rac)-[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide

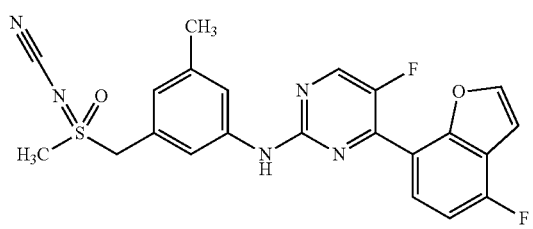

Preparation of Intermediate 13.1

3-(Chloromethyl)-5-methylaniline

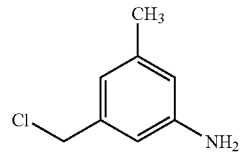

To a stirred solution of 3-amino-5-methyl-benzyl alcohol (5 g; 33.9 mmol; GL Syntech LLC, Hatfield, Pa.; CAS #146335-25-3; Behrens et al., Synthesis, 1992, 1235-6) in DCM (140 mL) at 0° C. was added dropwise thionyl chloride (7.4 mL; 102 mmol). The mixture was allowed to react at room temperature overnight. Then, the mixture was concentrated under reduced pressure. The resulting material was dissolved in DCM again and evaporated to dryness to give crude 3-(chloromethyl)-5-methylaniline (7 g).

Preparation of Intermediate 13.2

3-Methyl-5-[(methylsulfanyl)methyl]aniline

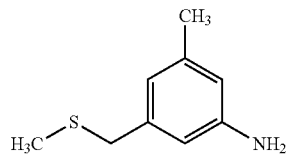

Intermediate 13.2 was prepared under similar conditions as described in the preparation of Intermediate 1.1 using 3-(chloromethyl)-5-methylaniline (Intermediate 13.1).

¹H NMR (400 MHz, DMSO-d₆) δ=6.33-6.27 (m, 1H), 6.27-6.21 (m, 2H), 4.95 (s, 2H), 3.47 (s, 2H), 2.12 (s, 3H), 1.94 (s, 3H).

Preparation of Intermediate 13.3

5-Fluoro-4-(4-fluoro-1-benzofuran-7-yl)-N-{3-methyl-5-[(methylsulfanyl)methyl]phenyl}pyrimidin-2-amine

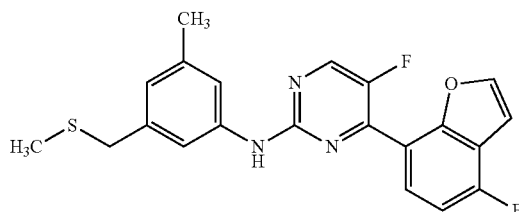

Intermediate 13.3 was prepared under similar conditions as described in the preparation of Intermediate 1.4 using 2-chloro-5-fluoro-4-(4-fluoro-1-benzofuran-7-yl)pyrimidine (Intermediate 1.3) and 3-methyl-5-[(methylsulfanyl)methyl]aniline (intermediate 13.2). The batch was purified by column chromatography on silica gel (hexanes/ethyl acetate) to give the title compound.

¹H NMR (400 MHz, DMSO-d₆) δ=9.77 (s, 1H), 8.71 (d, 1H), 8.20 (d, 1H), 7.76 (dd, 1H), 7.60 (s, 1H), 7.50 (s, 1H), 7.33 (dd, 1H), 7.23 (d, 1H), 6.71 (s, 1H), 3.59 (s, 2H), 2.25 (s, 3H), 1.94 (s, 3H).

Preparation of Intermediate 13.4 rac-[(3-{[5-Fluoro-4-(4-fluoro-1-benzofuran-7-yl)pyrimidin-2-yl]amino}-5-methylbenzyl)(methyl)-λ⁴-sulfanylidene]cyanamide

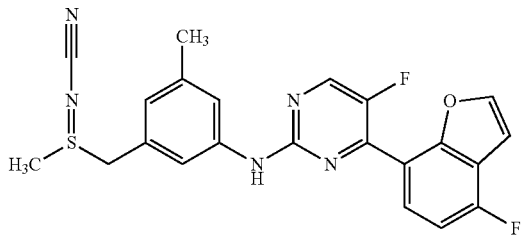

Intermediate 13.4 was prepared under similar conditions as described in the preparation of Intermediate 1.5 using 5-fluoro-4-(4-fluoro-1-benzofuran-7-yl)-N-{3-methyl-5-[(methylsulfanyl)-methyl]-phenyl}-pyrimidin-2-amine (Intermediate 13.3). The batch was purified by column chromatography on silica gel (hexanes/ethyl acetate).

¹H NMR (400 MHz, DMSO-d₆) δ=9.94 (s, 1H), 8.72 (d, 1H), 8.21 (d, 1H), 7.79 (dd, 1H), 7.66 (br. s., 2H), 7.34 (t, 1H), 7.23 (d, 1H), 6.84 (s, 1H), 4.39 (d, 1H), 4.21 (d, 1H), 2.83 (s, 3H), 2.29 (s, 3H).

Preparation of End Product:

Example 13 was prepared under similar conditions as described in the preparation of Example 1 using rac-[(3-{[5-fluoro-4-(4-fluoro-1-benzofuran-7-yl)pyrimidin-2-yl]amino}-5-methylbenzyl)(methyl)-λ⁴-sulfanylidene]cyanamide (310 mg; 0.71 mmol; Intermediate 13.4). The batch was purified by column chromatography on silica gel (hexane/ethyl acetate) to give the title compound (190 mg; 0.42 mmol).

¹H NMR (400 MHz, DMSO-d₆) δ=9.96 (s, 1H), 8.72 (d, 1H), 8.20 (d, 1H), 7.78 (dd, 1H), 7.71 (s, 2H), 7.33 (dd, 1H), 7.23 (d, 1H), 6.89 (s, 1H), 4.95-4.82 (m, 2H), 3.34 (s, 3H), 2.30 (s, 3H).

EXAMPLES 14 AND 15

Enantiomers of [(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide

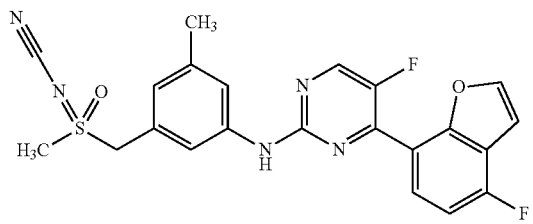 [SMILES: Cc1cc(CS(C)(=O)=NC#N)cc(Nc2ncc(F)c(-c3ccc(F)c4ccoc34)n2)c1]

(rac)-[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide (67 mg) was separated into the enantiomers by chiral preparative HPLC.

| System: | Agilent: Prep 1200, 2xPrep Pump, DLA, MWD, Prep FC |
|---|---|
| Column: | Chiralpak IC 5 μm 250 × 30 mm |
| Solvent: | hexane/ethanol 70/30 (v/v) |
| Flow: | 50 mL/min |
| Temperature: | RT |
| Solution: | 67.5 mg/1.5 mL EtOH/acetone |
| Injection: | 3 × 0.5 mL |
| Detection: | UV 280 nm |

| | Retention time in min | Amount | purity in % |
|---|---|---|---|
| Example 14 Enantiomer 1 | 8.1-10.3 | 27 mg | >99 |
| Example 15 Enantiomer 2 | 10.4-12.2 | 28 mg | 96 |

EXAMPLE 16

(rac)-5-Fluoro-4-(4-fluoro-1-benzofuran-7-yl)-N-{3-methyl-5-[(S-methylsulfonimidoyl)-methyl]phenyl}pyrimidin-2-amine

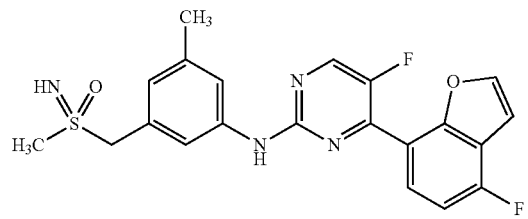

Example 16 was prepared under similar conditions as described in the preparation of Example 4 using (rac)-[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide (112 mg; 0.24 mmol; Example 13). The batch was purified by column chromatography on silica gel (ethyl acetate/MeOH) to give the title compound (46 mg; 0.09 mmol).

¹H NMR (400 MHz, DMSO-d₆) δ=9.83 (s, 1H), 8.70 (d, 1H), 8.21 (d, 1H), 7.77 (dd, 1H), 7.62 (d, 2H), 7.32 (dd, 1H), 7.23 (d, 1H), 6.83 (s, 1H), 4.31-4.20 (m, 2H), 3.51 (s, 1H), 2.77 (s, 3H), 2.28 (s, 3H).

EXAMPLE 17

(rac)-{[3-{[5-fluoro-4-(4-fluoro-1-benzofuran-7-yl)pyrimidin-2-yl]amino}-5-(pentafluoro-λ⁶-sulfanyl)benzyl](methyl)oxido-λ⁶-sulfanylidene}cyanamide

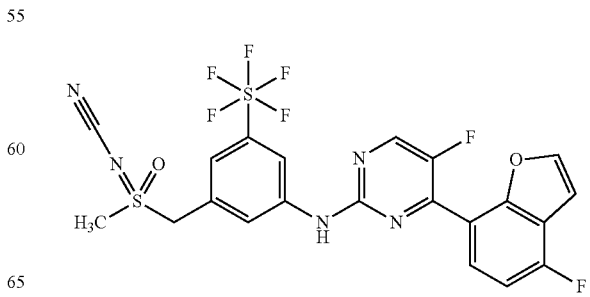

Preparation of Intermediate 17.1

3-Nitro-5-(pentafluoro-$\lambda^6$-sulfanyl)benzoic acid

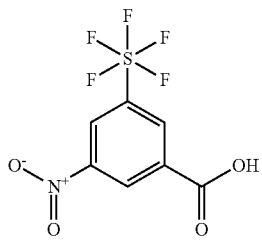 [SMILES: O=C(O)c1cc([N+](=O)[O-])cc(S(F)(F)(F)(F)F)c1]

Nitric acid (100%; 4.1 mL) was added dropwise over 30 minutes to a stirred solution of 3-(pentafluoro-$\lambda^6$-sulfanyl) benzoic acid (5.1 g; 20.6 mmol; ABCR GmbH & CO. KG) in sulfuric acid (17.0 mL) at 0° C. The ice bath was removed and the mixture was stirred for 88 hours at room temperature. The batch was cautiously added to ice. The precipitate was separated, washed with water and finally dissolved in ethyl acetate. The organic solution was washed with water, filtered using a Whatman filter and concentrated to give the desired product (4.4 g; 15.0 mmol).

$^1$H NMR (400 MHz, CDCl$_3$) δ=9.12 (s, 1H), 8.90 (m, 1H), 8.83 (m, 1H, 1H).

Preparation of Intermediate 17.2

[3-Nitro-5-(pentafluoro-$\lambda^6$-sulfanyl)phenyl]methanol

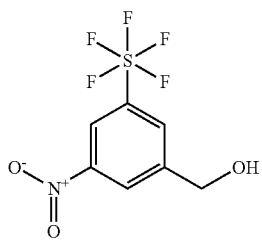 [SMILES: O=[N+]([O-])c1cc(CO)cc(S(F)(F)(F)(F)F)c1]

To a stirred solution of 3-nitro-5-(pentafluoro-$\lambda^6$-sulfanyl)benzoic acid (4.4 g; 15 mmol; Intermediate 17.1) in THF at 0° C. was added a μM solution of borane-tetrahydrofuran complex in THF (60 mL; 60 mmol). The mixture was allowed to react at ambient temperature for 19 hours. Then, MeOH was cautiously added to the stirred mixture while cooling with an ice bath. The batch was diluted with ethyl acetate and washed with aqueous sodium hydroxide solution (1N) and saturated aqueous sodium chloride solution. The organic layer was dried (sodium sulfate), filtered and concentrated to yield the title compound (5.14 g).

$^1$H NMR (400 MHz, CDCl$_3$) δ=8.54 (s, 1H), 8.42 (s, 1H), 8.12 (s, 1H), 4.92 (d, 2), 2.19 (tr, 1H).

Preparation of Intermediate 17.3

[3-Amino-5-(pentafluoro-$\lambda^6$-sulfanyl)phenyl]methanol

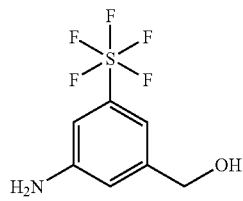

Intermediate 17.3 was prepared under similar conditions as described in the preparation of Intermediate 1.2 using [3-nitro-5-(pentafluoro-$\lambda^6$-sulfanyl)phenyl]methanol (Intermediate 17.2).

$^1$H NMR (400 MHz, CDCl$_3$) δ=7.11 (s, 1H), 6.96 (m, 1H), 6.81 (s, 1H), 4.66 (br, 2H), 3.89 (br, 2H).

Preparation of Intermediate 17.4

3-(Chloromethyl)-5-(pentafluoro-$\lambda^6$-sulfanyl)aniline

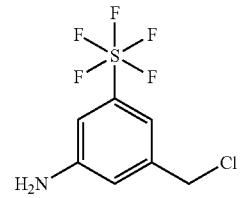 [SMILES: Nc1cc(CCl)cc(S(F)(F)(F)(F)F)c1]

Intermediate 17.4 was prepared under similar conditions as described in the preparation of Intermediate 13.1 using [3-amino-5-(pentafluoro-$\lambda^6$-sulfanyl)phenyl]methanol (Intermediate 17.3).

$^1$H NMR (400 MHz, DMSO-d$_6$) δ=7.01 (d, 2H), 6.84 (s, 1H), 5.74 (br.), 4.70 (s, 2H).

Preparation of Intermediate 17.5

3-[(Methylsulfanyl)methyl]-5-(pentafluoro-$\lambda^6$-sulfanyl)aniline

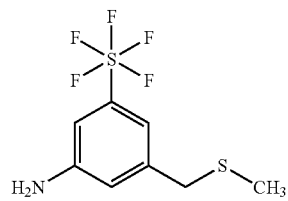

Intermediate 17.5 was prepared under similar conditions as described in the preparation of Intermediate 1.1 using 3-(chloromethyl)-5-(pentafluoro-$\lambda^6$-sulfanyl)aniline (Intermediate 17.4).

$^1$H NMR (400 MHz, DMSO-d$_6$) δ=6.92 (t, 1H), 6.87 (s, 1H), 6.73 (s, 1H), 5.67 (br. s., 2H), 3.63 (s, 2H), 1.96 (s, 3H).

Preparation of Intermediate 17.6

5-Fluoro-4-(4-fluoro-1-benzofuran-7-yl)-N-{3-[(methylsulfanyl)methyl]-5-(pentafluoro-λ$^6$-sulfanyl)phenyl}pyrimidin-2-amine

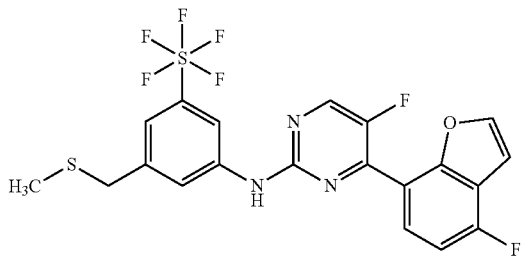 [SMILES: CSCc1cc(Nc2ncc(F)c(-c3ccc(F)c4ccoc34)n2)cc(S(F)(F)(F)(F)F)c1]

Intermediate 17.6 was prepared under similar conditions as described in the preparation of Intermediate 1.4 using 2-chloro-5-fluoro-4-(4-fluoro-1-benzofuran-7-yl)pyrimidine (Intermediate 1.3) and 3-[(Methylsulfanyl)methyl]-5-(pentafluoro-λ$^6$-sulfanyl)aniline (Intermediate 17.5). The batch was purified by column chromatography on silica gel (hexanes/ethyl acetate) to give the title compound.

$^1$H NMR (400 MHz, DMSO-d$_6$) δ=10.29 (s, 1H), 8.80 (d, 1H), 8.41 (t, 1H), 8.18 (d, 1H), 7.99 (s, 1H), 7.77 (dd, 1H), 7.42-7.38 (m, 1H), 7.36-7.29 (m, 1H), 7.24 (d, 1H), 3.76 (s, 2H), 1.95 (s, 3H).

Preparation of Intermediate 17.7

(rac)-[3-{[5-Fluoro-4-(4-fluoro-1-benzofuran-7-yl)pyrimidin-2-yl]amino}-5-(pentafluoro-λ$^6$-sulfanyl)benzyl](methyl)-λ$^4$-sulfanylidene]cyanamide

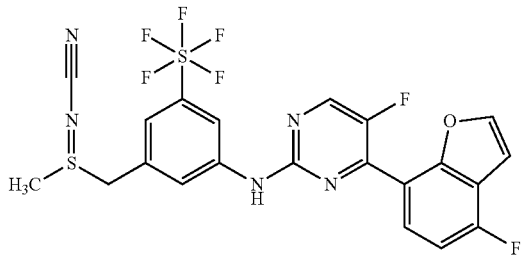 [SMILES: CS(Cc1cc(Nc2ncc(F)c(-c3ccc(F)c4ccoc34)n2)cc(S(F)(F)(F)(F)F)c1)=NC#N]

Intermediate 17.7 was prepared under similar conditions as described in the preparation of Intermediate 1.5 using 5-fluoro-4-(4-fluoro-1-benzofuran-7-yl)-N-{3-[(methylsulfanyl)methyl]-5-(pentafluoro-λ$^6$-sulfanyl)phenyl}pyrimidin-2-amine (Intermediate 17.6). The batch was purified by column chromatography on silica gel (ethyl acetate/MeOH).

$^1$H NMR (400 MHz, DMSO-d$_6$) δ=10.47 (s, 1H), 8.81 (d, 1H), 8.60 (t, 1H), 8.18 (d, 1H), 8.01 (s, 1H), 7.79 (dd, 1H), 7.55 (s, 1H), 7.34 (t, 1H), 7.24 (d, 1H), 4.62-4.32 (m, 2H), 2.87 (s, 3H).

Preparation of End Product:

Example 17 was prepared under similar conditions as described in the preparation of Example 1 using (rac)-[3-{[5-fluoro-4-(4-fluoro-1-benzofuran-7-yl)pyrimidin-2-yl]amino}-5-(pentafluoro-λ$^6$-sulfanyl)benzyl](methyl)-λ$^4$-sulfanylidene]cyanamide (205 mg; 0.373 mmol; Intermediate 17.7). The batch was purified by chromatography on silica gel (hexanes/ethyl acetate) to give the title compound (120 mg; 0.21 mmol).

$^1$H NMR (400 MHz, DMSO-d$_6$) δ=10.48 (s, 1H), 8.81 (d, 1H), 8.65 (s, 1H), 8.17 (d, 1H), 8.07 (s, 1H), 7.78 (dd, 1H), 7.59 (s, 1H), 7.33 (t, 1H), 7.23 (d, 1H), 5.18-5.08 (m, 2H), 3.42 (s, 3H).

EXAMPLE 18

(rac)-5-Fluoro-4-(4-fluoro-1-benzofuran-7-yl)-N-{3-[(S-methylsulfonimidoyl)methyl]-5-(pentafluoro-λ$^6$-sulfanyl)phenyl}pyrimidin-2-amine

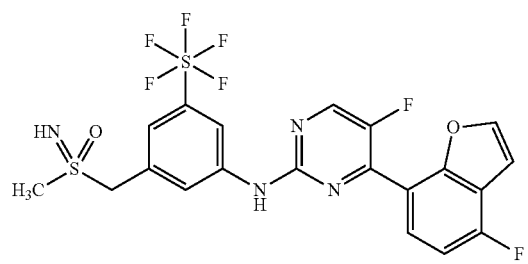 [SMILES: CS(=N)(=O)Cc1cc(Nc2ncc(F)c(-c3ccc(F)c4ccoc34)n2)cc(S(F)(F)(F)(F)F)c1]

Example 18 was prepared under similar conditions as described in the preparation of Example 4 using (rac)-{[3-{[5-fluoro-4-(4-fluoro-1-benzofuran-7-yl)pyrimidin-2-yl]amino}-5-(pentafluoro-λ$^6$-sulfanyl)-benzyl](methyl)oxido-λ$^6$-sulfanylidene}cyanamide (107 mg; 0.189 mmol; Example 17). The batch was purified by preparative HPLC to yield the title compound (24 mg; 0.04 mmol).

| System: | Waters Aqcuity UPLC-MS: Binary Solvent Manager, Sample Manager/Organizer, Column Manager, PDA, ELSD, SQD 3100 |
|---|---|
| Column: | Aqcuity BEH C18 1.7 50 × 2.1 mm |
| Solvent: | A = H$_2$O + 0.1% Vol. HCOOH (99%) |
| | B = acetonitrile |
| Gradient: | 0-1.6 min 1-99% B, 1.6-2.0 min 99% B |
| Flow: | 0.8 mL/min |
| Temperature: | 60° C. |
| Solution: | 1.0 mg/mL EtOH/MeOH 2:1 |
| Injektion: | 2.0 µl |
| Detection: | DAD TAC, scan range 210-400 nm |
| | MS ESI+, ESI−, scan range 160-1000 m/z |
| | ELSD |

$^1$H NMR (400 MHz, DMSO-d$_6$) δ=10.35 (s, 1H), 8.80 (d, 1H), 8.52 (t, 1H), 8.18 (d, 1H), 8.00 (s, 1H), 7.77 (dd, 1H), 7.56 (s, 1H), 7.32 (t, 1H), 7.24 (d, 1H), 4.46 (s, 2H), 3.71 (s, 1H), 2.81 (s, 3H).

The following Table 1 provides an overview on the compounds described in the example section:

TABLE 1

| Example No. | Structure | Name of compound |
|---|---|---|
| 1 | 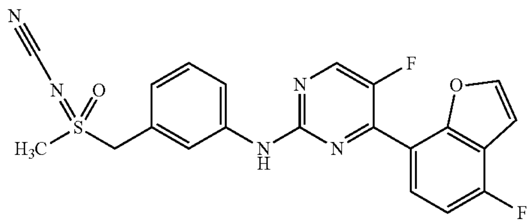 [SMILES: CS(=O)(Cc1cccc(Nc2ncc(F)c(-c3ccc(F)c4ccoc34)n2)c1)=NC#N] | (rac)-[(3-{[5-Fluoro-4-(4-fluoro-1-benzofuran-7-yl)pyrimidin-2-yl]amino}benzyl)(methyl)oxido-λ6-sulfanylidene]cyanamide |
| 2 | 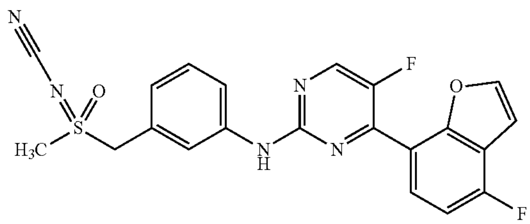 [SMILES: CS(=O)(Cc1cccc(Nc2ncc(F)c(-c3ccc(F)c4ccoc34)n2)c1)=NC#N] | [(3-{[5-Fluoro-4-(4-fluoro-1-benzofuran-7-yl)pyrimidin-2-yl]amino}benzyl)(methyl)oxido-λ6-sulfanylidene]cyanamide; Enantiomer 1 |
| 3 | 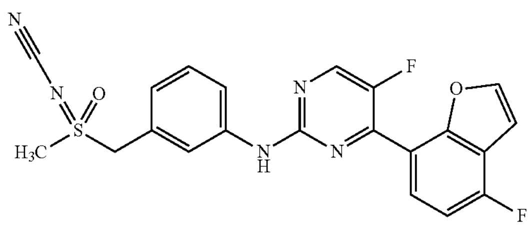 [SMILES: CS(=O)(Cc1cccc(Nc2ncc(F)c(-c3ccc(F)c4ccoc34)n2)c1)=NC#N] | [(3-{[5-Fluoro-4-(4-fluoro-1-benzofuran-7-yl)pyrimidin-2-yl]amino}benzyl)(methyl)oxido-λ6-sulfanylidene]cyanamide; Enantiomer 2 |
| 4 | 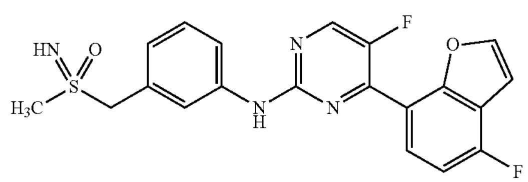 [SMILES: CS(=N)(=O)Cc1cccc(Nc2ncc(F)c(-c3ccc(F)c4ccoc34)n2)c1] | (rac)-5-Fluoro-4-(4-fluoro-1-benzofuran-7-yl)-N-{3-[(S-methylsulfonimidoyl)-methyl]phenyl}-pyrimidin-2-amine |
| 5 | 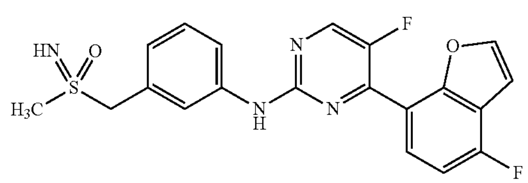 [SMILES: CS(=N)(=O)Cc1cccc(Nc2ncc(F)c(-c3ccc(F)c4ccoc34)n2)c1] | 5-Fluoro-4-(4-fluoro-1-benzofuran-7-yl)-N-{3-[(S-methylsulfonimidoyl)-methyl]-phenyl}-pyrimidin-2-amine; Enantiomer 1 |
| 6 | 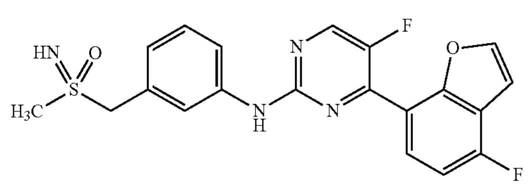 [SMILES: CS(=N)(=O)Cc1cccc(Nc2ncc(F)c(-c3ccc(F)c4ccoc34)n2)c1] | 5-Fluoro-4-(4-fluoro-1-benzofuran-7-yl)-N-{3-[(S-methylsulfonimidoyl)-methyl]-phenyl}-pyrimidin-2-amine; Enantiomer 2 |
| 7 | 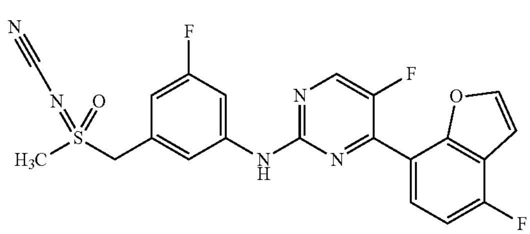 [SMILES: CS(=O)(Cc1cc(F)cc(Nc2ncc(F)c(-c3ccc(F)c4ccoc34)n2)c1)=NC#N] | (rac)-[(3-Fluoro-5-{[5-fluoro-4-(4-fluoro-1-benzofuran-7-yl)pyrimidin-2-yl]amino}benzyl)(methyl)-oxido-λ6-sulfanylidene]cyanamide |

TABLE 1-continued

| Example No. | Structure | Name of compound |
|---|---|---|
| 8 | 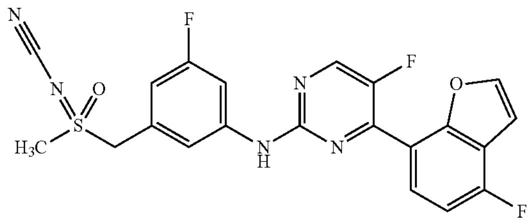 [SMILES: CS(=O)(Cc1cc(F)cc(Nc2ncc(F)c(-c3ccc(F)c4ccoc34)n2)c1)=NC#N] | [(3-Fluoro-5-{[5-fluoro-4-(4-fluoro-1-benzofuran-7-yl)pyrimidin-2-yl]amino}benzyl)(methyl)-oxido-$\lambda^6$-sulfanylidene]cyanamide; Enantiomer 1 |
| 9 | 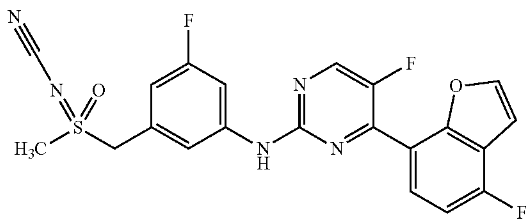 [SMILES: CS(=O)(Cc1cc(F)cc(Nc2ncc(F)c(-c3ccc(F)c4ccoc34)n2)c1)=NC#N] | [(3-Fluoro-5-{[5-fluoro-4-(4-fluoro-1-benzofuran-7-yl)pyrimidin-2-yl]amino}benzyl)(methyl)-oxido-$\lambda^6$-sulfanylidene]cyanamide; Enantiomer 2 |
| 10 | 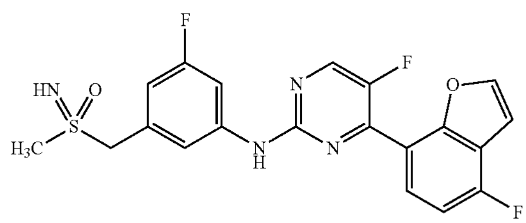 [SMILES: CS(=N)(=O)Cc1cc(F)cc(Nc2ncc(F)c(-c3ccc(F)c4ccoc34)n2)c1] | (rac)-5-Fluoro-4-(4-fluoro-1-benzofuran-7-yl)-N-{3-fluoro-5-[(S-methylsulfonimidoyl)-methyl]-phenyl}-pyrimidin-2-amine |
| 11 | 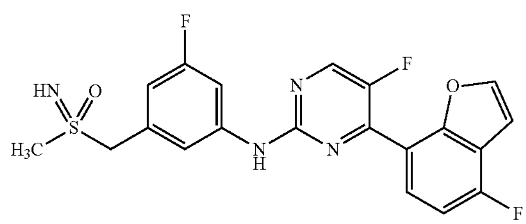 [SMILES: CS(=N)(=O)Cc1cc(F)cc(Nc2ncc(F)c(-c3ccc(F)c4ccoc34)n2)c1] | 5-Fluoro-4-(4-fluoro-1-benzofuran-7-yl)-N-{3-fluoro-5-[(S-methylsulfonimidoyl)-methyl]-phenyl}-pyrimidin-2-amine; Enantiomer 1 |
| 12 | 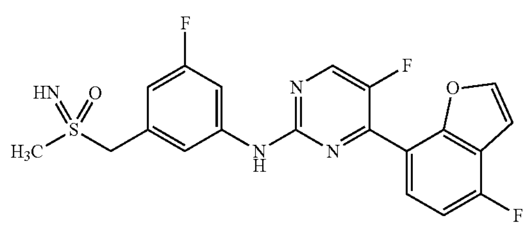 [SMILES: CS(=N)(=O)Cc1cc(F)cc(Nc2ncc(F)c(-c3ccc(F)c4ccoc34)n2)c1] | 5-Fluoro-4-(4-fluoro-1-benzofuran-7-yl)-N-{3-fluoro-5-[(S-methylsulfonimidoyl)-methyl]-phenyl}-pyrimidin-2-amine; Enantiomer 2 |
| 13 | 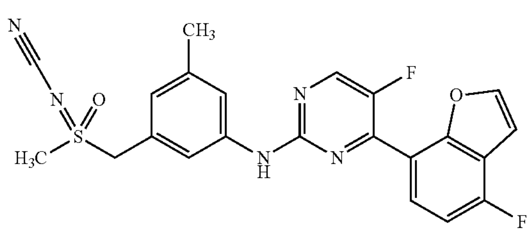 [SMILES: Cc1cc(CS(C)(=O)=NC#N)cc(Nc2ncc(F)c(-c3ccc(F)c4ccoc34)n2)c1] | (rac)-[(3-{[5-Fluoro-4-(4-fluoro-1-benzofuran-7-yl)pyrimidin-2-yl]amino}-5-methylbenzyl)-(methyl)oxido-$\lambda^6$-sulfanylidene]cyanamide |
| 14 | 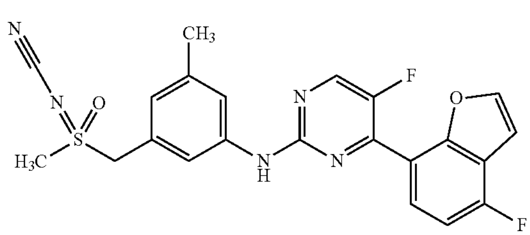 [SMILES: Cc1cc(CS(C)(=O)=NC#N)cc(Nc2ncc(F)c(-c3ccc(F)c4ccoc34)n2)c1] | [(3-{[5-Fluoro-4-(4-fluoro-1-benzofuran-7-yl)pyrimidin-2-yl]amino}-5-methylbenzyl)-(methyl)oxido-$\lambda^6$-sulfanylidene]cyanamide; Enantiomer 1 |

TABLE 1-continued

| Example No. | Structure | Name of compound |
| --- | --- | --- |
| 15 | 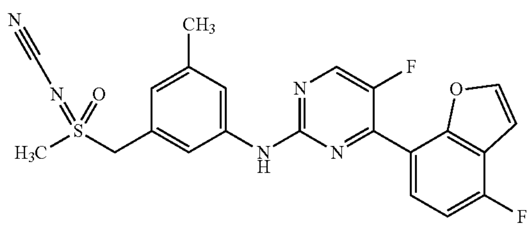 [SMILES: Cc1cc(CS(C)(=O)=NC#N)cc(Nc2ncc(F)c(-c3ccc(F)c4ccoc34)n2)c1] | [(3-{[5-Fluoro-4-(4-fluoro-1-benzofuran-7-yl)pyrimidin-2-yl]amino}-5-methylbenzyl)-(methyl)oxido-$\lambda^6$-sulfanylidene]cyanamide; Enantiomer 2 |
| 16 | 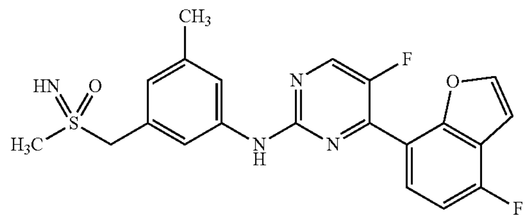 [SMILES: Cc1cc(CS(C)(=N)=O)cc(Nc2ncc(F)c(-c3ccc(F)c4ccoc34)n2)c1] | (rac)-5-Fluoro-4-(4-fluoro-1-benzofuran-7-yl)-N-{3-methyl-5-[(S-methylsulfonimidoyl)-methyl]phenyl}pyrimidin-2-amine |
| 17 | 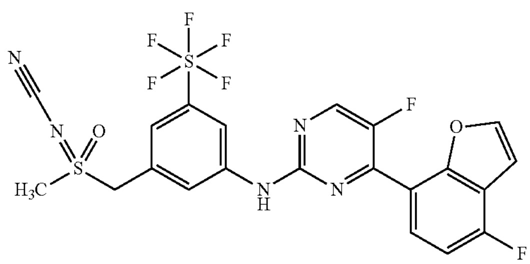 [SMILES: CS(=O)(Cc1cc(Nc2ncc(F)c(-c3ccc(F)c4ccoc34)n2)cc(S(F)(F)(F)(F)F)c1)=NC#N] | (rac)-{[3-{[5-fluoro-4-(4-fluoro-1-benzofuran-7-yl)pyrimidin-2-yl]amino}-5-(pentafluoro-$\lambda^6$-sulfanyl)benzyl](methyl)oxido-$\lambda^6$-sulfanylidene}cyanamide |
| 18 | 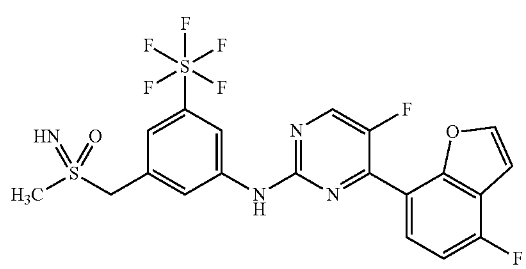 [SMILES: CS(=N)(=O)Cc1cc(Nc2ncc(F)c(-c3ccc(F)c4ccoc34)n2)cc(S(F)(F)(F)(F)F)c1] | (rac)-5-Fluoro-4-(4-fluoro-1-benzofuran-7-yl)-N-{3-[(S-methylsulfonimidoyl)methyl]-5-(pentafluoro-$\lambda^6$-sulfanyl)phenyl}pyrimidin-2-amine |

Results:

Table 2: Inhibition for CDK9 and CDK2 of compounds according to the present invention. The $IC_{50}$ (inhibitory concentration at 50% of maximal effect) values are indicated in nM, "n. t." means that the compounds have not been tested in the respective assay.

①: Example Number

②: CDK9: CDK9/CycT1 kinase assay as described under Method 1a. of Materials and Methods ③: CDK2: CDK2/CycE kinase assay as described under Method 2a. of Materials and Methods ④: Selectivity CDK9 over CDK2: $IC_{50}$ (CDK2)/$IC_{50}$ (CDK9) according to Methods 1a. and 2a. of Materials and Methods ⑤: high ATP CDK9: CDK9/CycT1 kinase assay as described under Method 1b. of Materials and Methods ⑥: high ATP CDK2: CDK2/CycE kinase assay as described under Method 2b. of Materials and Methods ⑦: Selectivity high ATP CDK9 over high ATP CDK2: $IC_{50}$ (high ATP CDK2)/$IC_{50}$ (high ATP CDK9) according to Methods 1b. and 2b. of Materials and Methods

TABLE 2

| ① | Structure | ② | ③ | ④ | ⑤ | ⑥ | ⑦ |
|---|---|---|---|---|---|---|---|
| 1 | (racemic) | 2.3 | 75 | 32 | 0.9 | 560 | 622 |
| 2 | (Enantiomer 1) | 1.4 | 19 | 14 | 1.1 | 353 | 321 |
| 3 | (Enantiomer 2) | 3.3 | 45 | 14 | 1.0 | 475 | 475 |
| 4 | (racemic) | 4.6 | 110 | 24 | 22 | 510 | 23 |
| 5 | (Enantiomer 1) | 3.7 | 89 | 24 | 5.6 | 802 | 143 |
| 6 | (Enantiomer 2) | 2.6 | 57 | 22 | 3.2 | 1000 | 313 |

TABLE 2-continued
| ① | Structure | ② | ③ | ④ | ⑤ | ⑥ | ⑦ |
|---|---|---|---|---|---|---|---|
| 7 | 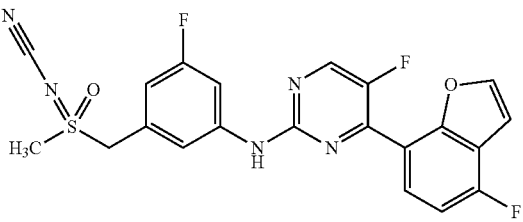 [SMILES: CS(=O)(Cc1cc(F)cc(Nc2ncc(F)c(-c3ccc(F)c4ccoc34)n2)c1)=NC#N] (racemic) | 4.1 | 56 | 14 | 1.9 | 652 | 343 |
| 8 | 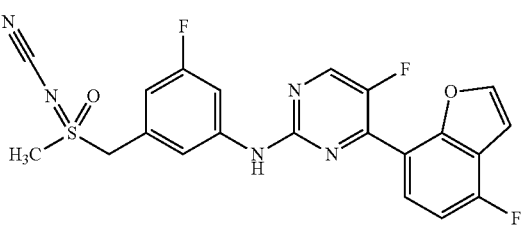 (Enantiomer 1) | 1.6 | 62 | 39 | 1 | 812 | 812 |
| 9 | 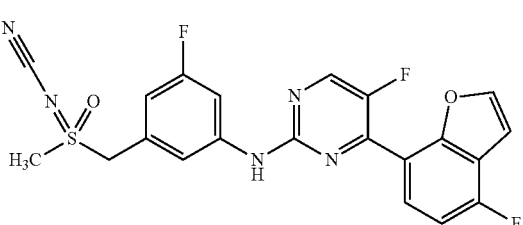 (Enantiomer 2) | 2.1 | 88 | 42 | 3.4 | 2230 | 656 |
| 10 | 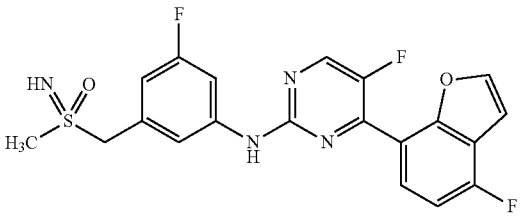 [SMILES: CS(=N)(=O)Cc1cc(F)cc(Nc2ncc(F)c(-c3ccc(F)c4ccoc34)n2)c1] (racemic) | 3.1 | 50 | 16 | 3.2 | 1800 | 563 |
| 11 | 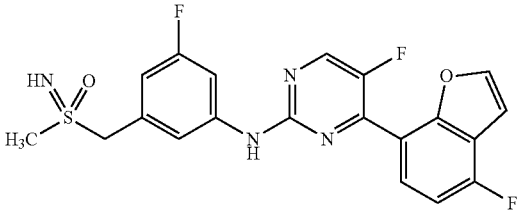 (Enantiomer 1) | n.t. | 73 | n.t. | 3.7 | 913 | 247 |
| 12 | 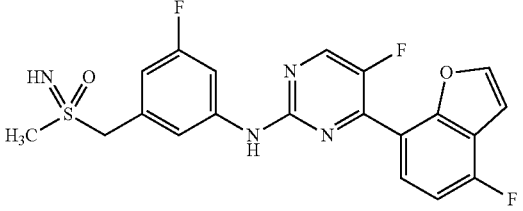 [SMILES: CS(=N)(=O)Cc1cc(F)cc(Nc2ncc(F)c(-c3ccc(F)c4ccoc34)n2)c1] (Enantiomer 2) | 3.1 | 48 | 15 | 0.99 | 1250 | 1263 |

TABLE 2-continued
| ① | Structure | ② | ③ | ④ | ⑤ | ⑥ | ⑦ |
|---|---|---|---|---|---|---|---|
| 13 | 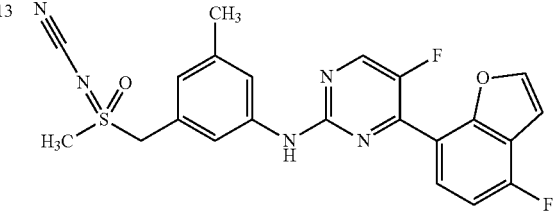 (racemic) | n.t. | 41 | n.t. | 0.88 | 1200 | 1364 |
| 14 | 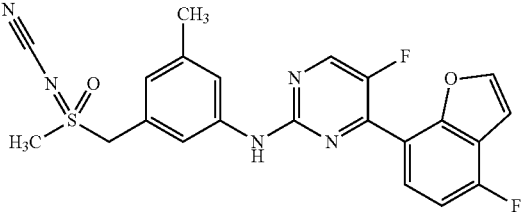 [SMILES: Cc1cc(CS(C)(=O)=NC#N)cc(Nc2ncc(F)c(-c3ccc(F)c4ccoc34)n2)c1] (Enantiomer 1) | 4.4 | 65 | 15 | 2.2 | 846 | 385 |
| 15 | 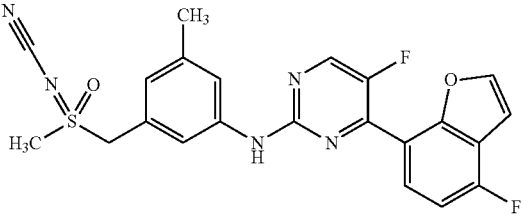 [SMILES: Cc1cc(CS(C)(=O)=NC#N)cc(Nc2ncc(F)c(-c3ccc(F)c4ccoc34)n2)c1] (Enantiomer 2) | 2.4 | 95 | 40 | 1.6 | 835 | 522 |
| 16 | 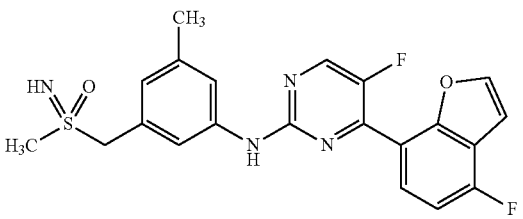 [SMILES: Cc1cc(CS(C)(=N)=O)cc(Nc2ncc(F)c(-c3ccc(F)c4ccoc34)n2)c1] (racemic) | 4.9 | 80 | 16 | 6.4 | 491 | 77 |
| 17 | 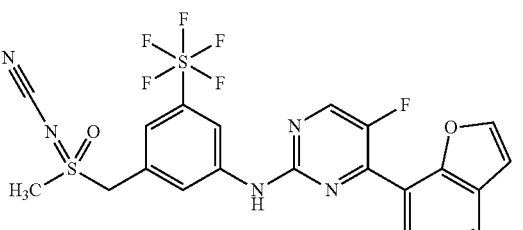 (racemic) | 8 | 257 | 33 | 7.4 | 1460 | 197 |

TABLE 2-continued

| ① Example | Structure | ② | ③ | ④ | ⑤ | ⑥ | ⑦ |
|---|---|---|---|---|---|---|---|
| 18 | [structure: 3-(pentafluorosulfanyl)-5-(methylsulfonimidoylmethyl)phenyl linked via NH to 5-fluoro-4-(4-fluorobenzofuran-7-yl)pyrimidin-2-yl] (racemic) | 2.9 | 73 | 25 | 4.4 | 1540 | 350 |

Table 3a and 3b:

Inhibition of proliferation of HeLa, HeLa-MaTu-ADR, NCI-H460, DU145, Caco-2, B16F10, A2780 and MOLM-13 cells (for corresponding indications see table 3a) by compounds according to the present invention, determined as described under Method 3. of Materials and Methods.

All $IC_{50}$ (inhibitory concentration at 50% of maximal effect) values are indicated in nM, "n.t." means that the compounds have not been tested in the respective assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of Bc6F10 cell proliferation
⑧: Inhibition of A2780 cell proliferation
⑨: Inhibition of MOLM-13 cell proliferation Said cell lines represent the following indications as shown in table 3a:

TABLE 3a

Indications represented by cell lines

| Cell line | Source | Indication |
|---|---|---|
| HeLa | ATCC | Human cervical tumour |
| HeLa-MaTu-ADR | EPO-GmbH Berlin | Multidrug-resistant human cervical carcinoma |
| NCI-H460 | ATCC | Human non-small cell lung carcinoma |
| DU 145 | ATCC | Hormone-independent human prostate carcinoma |
| Caco-2 | ATCC | Human colorectal carcinoma |
| B16F10 | ATCC | Mouse melanoma |
| A2780 | ECACC | Human ovarian carcinoma |
| MOLM-13 | DSMZ | Human acute myeloid leukemia |

TABLE 3b

Inhibition of cell proliferation

| ① | Structure | ② | ③ | ④ | ⑤ | ⑥ | ⑦ | ⑧ | ⑨ |
|---|---|---|---|---|---|---|---|---|---|
| 1 | [structure: N-cyano-S-methyl-S-(3-{[5-fluoro-4-(4-fluorobenzofuran-6-yl)pyrimidin-2-yl]amino}benzyl)sulfonimidoyl] (racemic) | 104 | 134 | 189 | 112 | 110 | 170 | 46 | 83 |
| 2 | [structure: same as above] (Enantiomer 1) | 100 | 87 | 117 | 54 | 87 | 75 | 55 | 29 |

TABLE 3b-continued

Inhibition of cell proliferation

| ① | Structure | ② | ③ | ④ | ⑤ | ⑥ | ⑦ | ⑧ | ⑨ |
|---|---|---|---|---|---|---|---|---|---|
| 3 | (Enantiomer 2) | | 109 | 118 | 188 | 105 | 144 | 136 | 67 | 47 |
| 4 | (racemic) | 297 | 143 | 181 | 169 | 141 | 211 | 53 | 108 |
| 5 | (Enantiomer 1) | | 177 | 190 | 343 | 186 | 230 | 260 | 93 | 115 |
| 6 | (Enantiomer 2) | | 115 | 96 | 314 | 110 | 112 | 185 | 38 | 117 |
| 7 | (racemic) | | 50 | 60 | 104 | 51 | 75 | 64 | 23 | 17 |
| 8 | (Enantiomer 1) | | 89 | 35 | 119 | 34 | 43 | 56 | 37 | 34 |

TABLE 3b-continued

Inhibition of cell proliferation

| ① | Structure | ② | ③ | ④ | ⑤ | ⑥ | ⑦ | ⑧ | ⑨ |
|---|---|---|---|---|---|---|---|---|---|
| 9 | (Enantiomer 2) | 31 | 42 | 106 | 34 | 54 | 52 | 19 | 24 |
| 10 | (racemic) | 97 | n.t. | 112 | 72 | 104 | 58 | 37 | 37 |
| 11 | (Enantiomer 1) | 31 | 200 | 83 | 41 | 47 | 45 | 32 | n.t. |
| 12 | (Enantiomer 2) | 30 | 88 | 59 | 62 | 57 | 94 | 35 | n.t. |
| 13 | (racemic) | 40 | 37 | 118 | 86 | 40 | 49 | 34 | n.t. |

TABLE 3b-continued

| ① | Structure | ② | ③ | ④ | ⑤ | ⑥ | ⑦ | ⑧ | ⑨ |
|---|---|---|---|---|---|---|---|---|---|
| 14 | (Enantiomer 1) | 96 | 57 | 112 | 66 | 61 | 69 | 45 | 75 |
| 15 | (Enantiomer 2) | 107 | 110 | 121 | 101 | 68 | 114 | 63 | 74 |
| 16 | (racemic) | 46 | 41 | 120 | 106 | 60 | 82 | 35 | 33 |
| 17 | (racemic) | 99 | 98 | 192 | 94 | 111 | 118 | 98 | 57 |
| 18 | (racemic) | 101 | 116 | 136 | 141 | 152 | 168 | 34 | 30 |

Table 4:

Caco-2 permeation of compounds according to the present invention, determined as described under Method 5. of Materials and Methods.

①: Example Number
②: Concentration of test compound indicated in μM.
③: $P_{app}$ A-B ($M_{art}$) indicated in [nm/s]
④: $P_{app}$ B-A ($M_{art}$) indicated in [nm/s]
⑤: Efflux ratio (Papp B-A/Papp A-B)

TABLE 4

| ① | Structure | ② | ③ | ④ | ⑤ |
|---|---|---|---|---|---|
| 4 | (racemic) | 2 | 183 | 104 | 0.57 |
| 6 | (Enantiomer 2) | 2 | 221 | 113 | 0.51 |

The invention claimed is:

1. A compound of formula (I)

(I)

wherein:

$R^1$ is a group selected from the group consisting of $C_1$-$C_6$-alkyl-, $C_3$-$C_7$-cycloalkyl-, heterocyclyl-, phenyl-, heteroaryl-, phenyl-$C_1$-$C_3$-alkyl-, and heteroaryl-$C_1$-$C_3$-alkyl-, wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, and —C(O)NH$_2$;

$R^2$ is the group

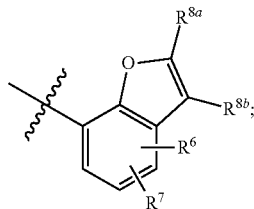

$R^3$ and $R^4$ are independently a group selected from the group consisting of a hydrogen atom, a fluoro atom, a chloro atom, a bromo atom, cyano, —SF$_5$, $C_1$-$C_3$-alkyl-, $C_1$-$C_3$-alkoxy-, halo-$C_1$-$C_3$-alkyl-, and $C_1$-$C_3$-fluoroalkoxy-;

$R^5$ is a group selected from the group consisting of a hydrogen atom, cyano, —C(O)R$^9$, —C(O)OR$^9$, —S(O)$_2$R$^9$, —C(O)NR$^{10}$R$^{11}$, —P(O)(OR$^{12}$)$_2$, —CH$_2$OP(OR$^{12}$)$_2$, $C_1$-$C_6$-alkyl-, $C_3$-$C_7$-cycloalkyl-, heterocyclyl-, phenyl-, and heteroaryl-, wherein said $C_1$-$C_6$-alkyl-, $C_3$-$C_7$-cycloalkyl-, heterocyclyl-, phenyl-, or heteroaryl-group is optionally substituted with one, two or three substituents, identically or differently, selected from the group consisting of halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

$R^6$ and $R^7$ are independently a group selected from the group consisting of a hydrogen atom, a fluoro atom, a chloro atom, $C_1$-$C_3$-alkyl-, $C_1$-$C_3$-alkoxy-, halo-$C_1$-$C_3$-alkyl-, and $C_1$-$C_3$-fluoroalkoxy-;

$R^{8a}$ and $R^{8b}$ are independently a group selected from the group consisting of a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^9$ is a group selected from the group consisting of $C_1$-$C_6$-alkyl-, halo-$C_1$-$C_3$-alkyl-, $C_3$-$C_7$-cycloalkyl-, heterocyclyl-, phenyl-, benzyl-, and heteroaryl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

$R^{10}$ and $R^{11}$ are independently a group selected from the group consisting of a hydrogen atom, $C_1$-$C_6$-alkyl-, $C_3$-$C_7$-cycloalkyl-, heterocyclyl-, phenyl-, benzyl-, and heteroaryl-, wherein said $C_1$-$C_6$-alkyl-, $C_3$-$C_7$-cycloalkyl-, heterocyclyl-, phenyl-, benzyl-, or heteroaryl- group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, and $C_1$-$C_3$-fluoroalkoxy-; or $R^{10}$ and $R^{11}$ are taken together with the nitrogen atom to which they are attached to form a cyclic amine; and $R^{12}$ is a group selected from the group consisting of a hydrogen atom, $C_1$-$C_4$-alkyl- and benzyl-, or an enantiomer, a diastereomer, a salt, a solvate, or a salt of a solvate thereof.

2. The compound of formula (I) according to claim 1, wherein:

$R^1$ is a group selected from the group consisting of $C_1$-$C_6$-alkyl- and $C_3$-$C_5$-cycloalkyl-, wherein said group is optionally substituted with one substituent selected from the group consisting of hydroxy, halo-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(O)(OH)$_2$, —C(O)OH, and —C(O)NH$_2$;

$R^2$ is the group

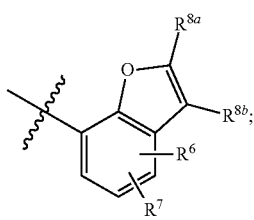

$R^3$ is a hydrogen atom, a fluoro atom, a chloro atom, a —$SF_5$ group, a $C_1$-$C_3$-alkyl- group, or a fluoro-$C_1$-$C_3$-alkyl- group;

$R^4$ is a hydrogen atom or a fluoro atom;

$R^5$ is a group selected from the group consisting of a hydrogen atom, cyano, —C(O)$R^9$, —C(O)O$R^9$, —S(O)$_2R^9$, —C(O)N$R^{10}R^{11}$, —P(O)(O$R^{12}$)$_2$, —CH$_2$OP(O$R^{12}$)$_2$, $C_1$-$C_6$-alkyl-, $C_3$-$C_7$-cycloalkyl-, heterocyclyl-, phenyl-, and heteroaryl-, wherein said $C_1$-$C_6$-alkyl-, $C_3$-$C_7$-cycloalkyl-, heterocyclyl-, phenyl-, or heteroaryl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

$R^6$ and $R^7$ are independently a group selected from the group consisting of a hydrogen atom, a fluoro atom, a chloro atom, $C_1$-$C_3$-alkyl-, $C_1$-$C_3$-alkoxy-, halo-$C_1$-$C_3$-alkyl-, and $C_1$-$C_3$-fluoroalkoxy-;

$R^{8a}$ and $R^{8b}$ are independently a group selected from the group consisting of a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^9$ is a group selected from the group consisting of $C_1$-$C_6$-alkyl-, halo-$C_1$-$C_3$-alkyl-, $C_3$-$C_7$-cycloalkyl-, heterocyclyl-, phenyl-, benzyl-, and heteroaryl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

$R^{10}$ and $R^{11}$ represent, independently from each other, are independently a group selected from the group consisting of a hydrogen atom, $C_1$-$C_6$-alkyl-, $C_3$-$C_7$-cycloalkyl-, heterocyclyl-, benzyl-, phenyl-, and heteroaryl-, wherein said $C_1$-$C_6$-alkyl-, $C_3$-$C_7$-cycloalkyl-, heterocyclyl-, benzyl-, phenyl-, or heteroaryl- group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, and $C_1$-$C_3$-fluoroalkoxy-; or $R^{10}$ and $R^{11}$ are taken together with the nitrogen atom to which they are attached to form a cyclic amine; and $R^{12}$ is a group selected from the group consisting of a hydrogen atom and $C_1$-$C_2$-alkyl-;

or an enantiomer, a diastereomer, a salt, a solvate, or a salt of a solvate thereof.

3. The compound of formula (I) according to claim 1, wherein:

$R^1$ is a group selected from the group consisting of $C_1$-$C_6$-alkyl- and $C_3$-$C_5$-cycloalkyl-, wherein said group is optionally substituted with one substituent selected from the group consisting of hydroxy, $C_1$-$C_3$-alkoxy-, —$NH_2$, alkylamino-, dialkylamino-, cyclic amines, and —OP(O)(OH)$_2$;

$R^2$ is the group

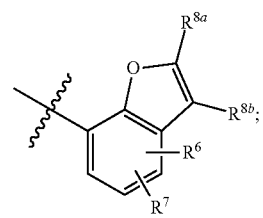

$R^3$ is a hydrogen atom, a fluoro atom, a chloro atom, a —$SF_5$ group, a $C_1$-$C_3$-alkyl- group, or a fluoro-$C_1$-$C_3$-alkyl- group;

$R^4$ is a hydrogen atom or a fluoro atom;

$R^5$ is a group selected from the group consisting of a hydrogen atom, cyano, —C(O)$R^9$, —C(O)O$R^9$, —C(O)N$R^{10}R^{11}$, P(O)(O$R^{12}$)$_2$, —CH$_2$OP(O$R^{12}$)$_2$, and $C_1$-$C_3$-alkyl-, wherein said $C_1$-$C_3$-alkyl group is optionally substituted with one substituent selected from the group consisting of —$NH_2$, alkylamino-, dialkylamino-, and cyclic amines;

$R^6$ and $R^7$ are independently a group selected from the group consisting of a hydrogen atom, a fluoro atom and a chloro atom;

$R^{8a}$ and $R^{8b}$ are independently a group selected from the group consisting of a hydrogen atom, a fluoro atom, a chloro atom, a bromo atom, cyano, methyl-, methoxy-, halomethyl-, and fluoromethoxy-;

$R^9$ is a group selected from the group consisting of $C_1$-$C_3$-alkyl-, halo-$C_1$-$C_3$-alkyl-, and benzyl- group, the phenyl- group of which is optionally substituted with one or two substituents, identically or differently, selected from the group consisting of halogen, $C_1$-$C_3$-alkyl-, $C_1$-$C_3$-alkoxy-, —$NH_2$, alkylamino-, and dialkylamino-;

$R^{10}$ and $R^{11}$ are independently a group selected from the group consisting of a hydrogen atom, $C_1$-$C_3$-alkyl-, and benzyl-;
or
$R^{10}$ and $R^{11}$ are taken together with the nitrogen atom to which they are attached to form a cyclic amine; and $R^{12}$ is a group selected from the group consisting of a hydrogen atom and methyl-,
or an enantiomer, a diastereomer, a salt, a solvate, or a salt of a solvate thereof.

4. The compound of formula (I) according to claim 1, wherein:
$R^1$ is a $C_1$-$C_6$-alkyl- group,
wherein said group is optionally substituted with one substituent, selected from the group consisting of $C_1$-$C_3$-alkoxy, —$NH_2$, alkylamino-, dialkylamino-, and cyclic amines;

$R^2$ is the group

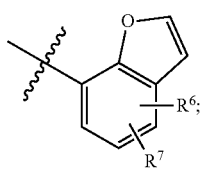

$R^3$ is a hydrogen atom, a fluoro atom, a chloro atom, a —$SF_5$ group, a methyl-group, an ethyl- group, or a trifluoromethyl- group;

$R^4$ is a hydrogen atom or a fluoro atom;

$R^5$ is a group selected from the group consisting of a hydrogen atom, cyano, —C(O)$R^9$, —C(O)O$R^9$, and —C(O)N$R^{10}R^{11}$;

$R^6$ and $R^7$ are independently a group selected from the group consisting of a hydrogen atom, a fluoro atom, and a chloro atom;

$R^9$ is a $C_1$-$C_3$-alkyl- group, a benzyl- group, or trifluoromethyl-; and $R^{10}$ and $R^{11}$ are independently a group selected from the group consisting of a hydrogen atom and $C_1$-$C_2$-alkyl-,
or an enantiomer, a diastereomer, a salt, a solvate, or a salt of a solvate thereof.

5. The compound of formula (I) according to claim 1, wherein:
$R^1$ is a $C_1$-$C_3$-alkyl- group;

$R^2$ is the group

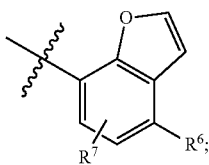

$R^3$ is a hydrogen atom, a fluoro atom, a methyl- group, or a —$SF_5$ group;

$R^4$ is a hydrogen atom;

$R^5$ is a group selected from the group consisting of a hydrogen atom, cyano, —C(O)$R^9$, —C(O)O$R^9$, and —C(O)N$R^{10}R^{11}$;

$R^6$ is a group selected from the group consisting of a hydrogen atom and a fluoro atom;

$R^7$ is a hydrogen atom;

$R^9$ is a methyl- group, an ethyl- group, or a trifluoroethyl- group;

$R^{10}$ is a $C_1$-$C_2$-alkyl- group; and $R^{11}$ is a hydrogen atom,
or an enantiomer, a diastereomer, a salt, a solvate, or a salt of a solvate thereof.

6. The compound of formula (I) according to claim 1, wherein:
$R^2$ is the group

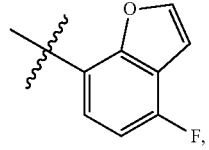

or an enantiomer, a diastereomer, a salt, a solvate, or a salt of a solvate thereof.

7. The compound of formula (I) according to claim 1, wherein
$R^5$ is a group selected from the group consisting of a hydrogen atom and a cyano group,
or an enantiomer, a diastereomer, a salt, a solvate, or a salt of a solvate thereof.

8. The compound of formula (I) according to claim 1, wherein
$R^3$ is a hydrogen atom, a fluoro atom, a methyl- group, or a —$SF_5$ group; and
$R^4$ is a hydrogen atom,
or an enantiomer, a diastereomer, a salt, a solvate, or a salt of a solvate thereof.

9. The compound of formula (I) according to claim 1, wherein:
$R^1$ is a methyl- group;
$R^2$ is the group

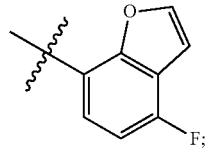 [SMILES: *c1ccc(F)c2ccoc12]

$R^3$ is a hydrogen atom, a fluoro atom, a methyl- group, or a —$SF_5$ group;

$R^4$ is a hydrogen atom; and

R⁵ is a group selected from the group consisting of a hydrogen atom and a cyano group,
or an enantiomer, a diastereomer, a salt, a solvate, or a salt of a solvate thereof.

10. The compound according to claim 1, which is selected from the group consisting of:
(rac)-[(3-{[5-Fluoro-4-(4-fluoro-1-benzofuran-7-yl)pyrimidin-2-yl]amino}benzyl)(methyl)oxido-λ⁶-sulfanylidene]cyanamide;
[(3-{[5-Fluoro-4-(4-fluoro-1-benzofuran-7-yl)pyrimidin-2-yl]amino}benzyl)(methyl)oxido-λ⁶-sulfanylidene]cyanamide, Enantiomer 1;
[(3-{[5-Fluoro-4-(4-fluoro-1-benzofuran-7-yl)pyrimidin-2-yl]amino}benzyl)(methyl)oxido-λ⁶-sulfanylidene]cyanamide Enantiomer 2;
(rac)-5-Fluoro-4-(4-fluoro-1-benzofuran-7-yl)-N-{3-[(S-methylsulfonimidoyl)-methyl]phenyl}-pyrimidin-2-amine;
5-Fluoro-4-(4-fluoro-1-benzofuran-7-yl)-N-{3-[(S-methylsulfonimidoyl)-methyl]-phenyl}-pyrimidin-2-amine Enantiomer 1;
5-Fluoro-4-(4-fluoro-1-benzofuran-7-yl)-N-{3-[(S-methylsulfonimidoyl)-methyl]-phenyl}-pyrimidin-2-amine Enantiomer 2;
(rac)-[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide;
[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide Enantiomer 1;
[(3-Fluoro-5-{[5-fluoro-4-(4-fluoro-1-benzofuran-7-yl)pyrimidin-2-yl]amino}benzyl)(methyl)-oxido-λ⁶-sulfanylidene]cyanamide Enantiomer 2;
(rac)-5-Fluoro-4-(4-fluoro-1-benzofuran-7-yl)-N-{3-fluoro-5-[(S-methylsulfonimidoyl)-methyl]-phenyl}-pyrimidin-2-amine;
5-Fluoro-4-(4-fluoro-1-benzofuran-7-yl)-N-{3-fluoro-5-[(S-methylsulfonimidoyl)-methyl]-phenyl}-pyrimidin-2-amine Enantiomer 1;
5-Fluoro-4-(4-fluoro-1-benzofuran-7-yl)-N-{3-fluoro-5-[(S-methylsulfonimidoyl)-methyl]-phenyl}-pyrimidin-2-amine Enantiomer 2;
(rac)-[(3-{[5-Fluoro-4-(4-fluoro-1-benzofuran-7-yl)pyrimidin-2-yl]amino}-5-methylbenzyl)-(methyl)oxido-λ6-sulfanylidene]cyanamide;
[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide Enantiomer 1;
[(3-{[5-Fluoro-4-(4-fluoro-1-benzofuran-7-yl)pyrimidin-2-yl]amino}-5-methylbenzyl)-(methyl)oxido-λ⁶-sulfanylidene]cyanamide Enantiomer 2;
(rac)-5-Fluoro-4-(4-fluoro-1-benzofuran-7-yl)-N-{3-methyl-5-[(S-methylsulfonimidoyl)-methyl]phenyl}pyrimidin-2-amine;
(rac)-{[3-{[5-fluoro-4-(4-fluoro-1-benzofuran-7-yl)pyrimidin-2-yl]amino}-5-(pentafluoro-λ⁶-sulfanyl)benzyl](methyl)oxido-λ⁶-sulfanylidene}cyanamide; and
(rac)-5-Fluoro-4-(4-fluoro-1-benzofuran-7-yl)-N-{3-[(S-methylsulfonimidoyl)methyl]-5-(pentafluoro-λ⁶-sulfanyl)phenyl}pyrimidin-2-amine,
or an enantiomer, a diastereomer, a salt, a solvate, or a salt of a solvate thereof.

11. A method for treatment of lung carcinoma, prostate carcinoma, cervical carcinoma, colorectal carcinoma, melanoma, ovarian carcinoma, or leukemia, comprising administering to a subject in need thereof an effective amount of the compound of formula (I) according to claim 1, or an enantiomer, a diastereomer, a salt, a solvate, or a salt of a solvate thereof.

12. A method for treatment of non-small cell lung carcinoma, hormone-independent human prostate carcinoma, cervical carcinoma, multidrug-resistant human cervical carcinoma, colorectal carcinoma, melanoma, ovarian carcinoma, or acute myeloid leukemia, comprising administering to a subject in need thereof an effective amount of the compound of formula (I) according to claim 1, or an enantiomer, a diastereomer, a salt, a solvate, or a salt of a solvate thereof.

13. A pharmaceutical combination comprising the compound of formula (I) according to claim 1, or an enantiomer, a diastereomer, a salt, a solvate, or a salt of a solvate thereof, in combination with at least one or more additional active ingredients.

14. A pharmaceutical composition comprising the compound of formula (I) according to claim 1, or an enantiomer, a diastereomer, a salt, a solvate, or a salt of a solvate thereof, in combination with an inert, nontoxic, pharmaceutically suitable adjuvant.

15. A method for treatment of lung carcinoma, prostate carcinoma, cervical carcinoma, colorectal carcinoma, melanoma, ovarian carcinoma, or leukemia, comprising administering to a subject in need thereof the pharmaceutical combination according to claim 13.

16. A method for treatment of lung carcinoma, prostate carcinoma, cervical carcinoma, colorectal carcinoma, melanoma, ovarian carcinoma, or leukemia, comprising administering to a subject in need thereof the pharmaceutical combination according to claim 14.

17. A compound of formula (6)

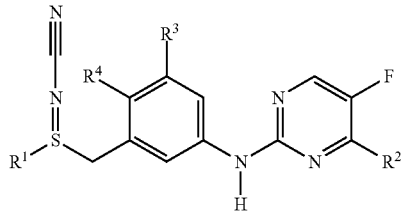

wherein,
R¹ is a group selected from the group consisting of $C_1$-$C_6$-alkyl-, $C_3$-$C_7$-cycloalkyl-, heterocyclyl-, phenyl-, heteroaryl-, phenyl-$C_1$-$C_3$-alkyl-, and heteroaryl-$C_1$-$C_3$-alkyl-,
wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, —NH₂, alkylamino-, dialkylamino-, acetylamino-, N-methyl-N-acetylamino-, cyclic amines, —OP(O)(OH)₂, —C(O)OH, and —C(O)NH₂;

$R^2$ is the group

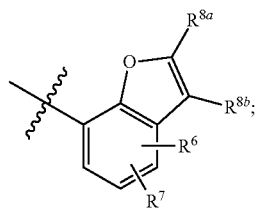

$R^3$ and $R^4$ are independently a group selected from the group consisting of a hydrogen atom, a fluoro atom, a chloro atom, a bromo atom, cyano, —$SF_5$, $C_1$-$C_3$-alkyl-, $C_1$-$C_3$-alkoxy-, halo-$C_1$-$C_3$-alkyl-, and $C_1$-$C_3$-fluoroalkoxy-;

$R^6$ and $R^7$ are independently a group selected from the group consisting of a hydrogen atom, a fluoro atom, a chloro atom, $C_1$-$C_3$-alkyl-, $C_1$-$C_3$-alkoxy-, halo-$C_1$-$C_3$-alkyl-, and $C_1$-$C_3$-fluoroalkoxy-; and $R^{8a}$ and $R^{8b}$ are independently a group selected from the group consisting of a hydrogen atom, a fluoro atom, a chloro atom, a bromo atom, cyano, $C_1$-$C_3$-alkyl-, $C_1$-$C_3$-alkoxy-, halo-$C_1$-$C_3$-alkyl-, and $C_1$-$C_3$-fluoroalkoxy-, or an enantiomer, a diastereomer, a salt, a solvate, or a salt of a solvate thereof.

18. A process for preparing the compound of formula (I) according to claim 1, comprising oxidizing a compound of formula (6)

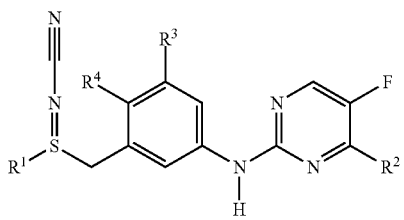

wherein $R^1$, $R^2$, $R^3$ and $R^4$ are as defined according to claim 1 for the compound of general formula (I), with an oxidation agent to give a compound of formula (7)

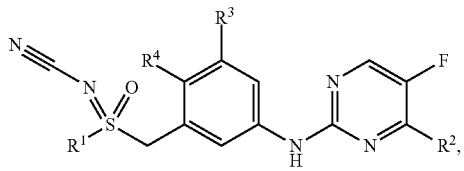

wherein $R^1$, $R^2$, $R^3$ and $R^4$ are as defined according to claim 1;

reacting the compound of formula (7) with trifluoroacetic anhydride followed by addition of a base to give a compound of formula (8)

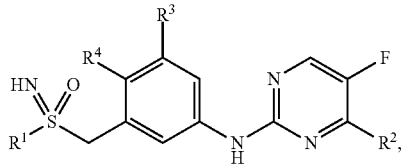

wherein $R^1$, $R^2$, $R^3$ and $R^4$ are as defined according to claim 1; and reacting the compound of formula (8) with an alkylation, acylation, arylation, isocyanate, sulfonylchloride, or chloroformiate agent, or with bromocyane, to give the compound of formula (I)

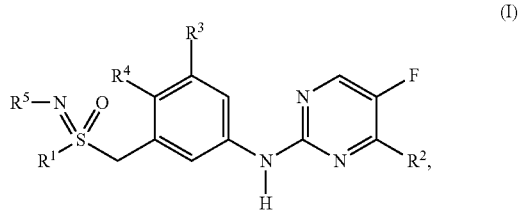

wherein $R^1$, $R^2$, $R^3$, $R^4$, and $R^5$ are as defined according to claim 1.

19. The compound according to claim 1 or a salt thereof.

20. The compound according to claim 10 or a salt thereof.

21. The method according to claim 12, comprising administering the compound of formula (I) or a salt thereof.

22. The pharmaceutical combination of claim 13, comprising the compound of formula (I) or a salt thereof.

23. The pharmaceutical composition of claim 14, comprising the compound of formula (I) or a salt thereof.

\* \* \* \* \*